United States Patent
Belair et al.

(10) Patent No.: US 10,183,079 B2
(45) Date of Patent: Jan. 22, 2019

(54) HYDROGEL MICROSPHERES CONTAINING PEPTIDE LIGANDS FOR GROWTH FACTOR REGULATION IN BLOOD PRODUCTS

(71) Applicant: Wisconsin Alumni Research Foundation, Madison, WI (US)

(72) Inventors: David Belair, Madison, WI (US); Ngoc Nhi Le, Norcross, GA (US); Michael W. Toepke, Midland, MI (US); Nicholas Impellitteri, Madison, WI (US); Connie Sue Chamberlain, Monona, WI (US); William Leo Murphy, Waunakee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/074,493

(22) Filed: Mar. 18, 2016

(65) Prior Publication Data

US 2017/0266318 A1    Sep. 21, 2017

(51) Int. Cl.
| | | |
|---|---|---|
| *A61K 38/17* | (2006.01) | |
| *A61K 47/48* | (2006.01) | |
| *A61K 47/60* | (2017.01) | |
| *A61K 47/69* | (2017.01) | |

(52) U.S. Cl.
CPC ...... *A61K 47/48784* (2013.01); *A61K 38/179* (2013.01); *A61K 47/48215* (2013.01); *A61K 47/60* (2017.08); *A61K 47/6903* (2017.08); *A61K 47/6927* (2017.08); *C07K 2319/30* (2013.01); *C07K 2319/32* (2013.01)

(58) Field of Classification Search
None
See application file for complete search history.

(56) References Cited

PUBLICATIONS

Holmes et al. ("Vascular endothelial growth factor receptor-2: Structure, function, intracellular signaling and therapeutic inhibition" Cellular Signaling 19 (2007) 2003-2012).*
Of Sigma-Aldrich (8arm-PEG20K-Norbornene, tripentaerythritol core, Dec. 11, 2014).*
Parlato et al. (Acta biomater. Dec. 2013; 9(12):9270-9280).*
Belair et al., Serum-Dependence of Affintiy-Mediated VEGF Release from Biomimetic Microspheres, American Chemical Society, 2014, pp. 2038-2048.
Fairbanks et al., A Versatile Synthetic Extracellular Matrix Mimic via Thiol-Norbornene Photopolymerization, Adv Mater, 2009, vol. 21, No. 48, pp. 5005-5010.
Impellitteri et al., Specific VEGF sequestering and release using peptide-functionalized hydrogel microspheres, Biomaterials, 2012, vol. 33, No. 12, pp. 2475-3484.
Toepke et al., Regulating specific growth factor signaling using immobilized branched ligands, Adv Healthc Mater., 2012, vol. 1, No. 4, pp. 457-460.

* cited by examiner

*Primary Examiner* — Jennifer Pitrak McDonald
*Assistant Examiner* — Tara L Martinez
(74) *Attorney, Agent, or Firm* — Stinson Leonard Street LLP

(57) ABSTRACT

Vascular endothelial growth factor VEGF-sequestering hydrogel microspheres that have been prepared to selectively bind VEGF from blood products are disclosed herein. In one particular embodiment, the microspheres bind VEGF as part of an intra-operative process such that the growth factor can be removed from the blood products before the products are used in a clinical procedure.

13 Claims, 21 Drawing Sheets

Specification includes a Sequence Listing.

US 10,183,079 B2

HYDROGEL MICROSPHERES CONTAINING PEPTIDE LIGANDS FOR GROWTH FACTOR REGULATION IN BLOOD PRODUCTS

STATEMENT OF GOVERNMENT SUPPORT

This invention was made with government support under HL093282 awarded by the National Institutes of Health. The Government has certain rights in the invention.

INCORPORATION OF SEQUENCE LISTING

A paper copy of the Sequence Listing and a computer readable form of the Sequence Listing containing the file named "P160179_ST25.txt", which is 6,685 bytes in size (as measured in MICROSOFT WINDOWS® EXPLORER), are provided herein and are herein incorporated by reference. This Sequence Listing consists of SEQ ID NOs:1-12.

BACKGROUND OF THE DISCLOSURE

The present disclosure relates generally to hydrogel microspheres for use in removing or otherwise reducing the activity of growth factors from blood products. Particularly, vascular endothelial growth factor (VEGF)-sequestering hydrogel microspheres have been prepared to selectively bind VEGF from blood products, thereby regulating VEGF activity for applications wherein VEGF activity may be deleterious for wound healing. In one particular embodiment, the microspheres bind VEGF as part of an intra-operative process such that the growth factor can be removed from the blood products before the products are used in a clinical procedure.

Angiogenesis during wound healing involves a complex interplay of vascular and stromal cells, the extracellular matrix, and platelets that are activated upon wound healing stimuli. Platelet activation initiates growth factor release and subsequent growth factor signaling to cells in the wound healing milieu. For example, activated platelets release vascular endothelial growth factor (VEGF), which signals to vascular endothelial cells (ECs) and initiates angiogenic sprouting during early wound healing. VEGF must be maintained in a limited concentration range to initiate angiogenesis during wound healing and ultimately to form patent new vasculature. Unregulated VEGF expression often results in hemangioma formation in vivo, and high levels of VEGF activity promote aberrant angiogenesis associated with poor musculoskeletal wound healing and disease pathology, including ocular disease.

The native extracellular matrix (ECM) modulates the cell response to VEGF, and synthetic biomaterials designed to mimic the ECM can regulate VEGF activity in culture and in vivo. For example, VEGF loaded hydrogels containing heparin binding peptide amphiphiles potentiated VEGF signaling in culture and in vivo, and VEGF loaded hydrogels containing fibronectin-mimicking peptides increased VEGF-dependent EC function in vitro and increased neovascularization in vivo. Fibronectin and heparin, however, can promiscuously bind multiple growth factors, and are thus limited in their ability to regulate VEGF with specificity.

Based on the foregoing, there is a need in the art for a synthetic biomaterial that can regulate growth factors, and regulate VEGF selectively, such to allow improved wound healing. It would be particularly advantageous if the biomaterial could remove VEGF from solution, such as autologous blood products, allowing for intra-operative processing of blood products before the products are used in clinical procedures.

BRIEF DESCRIPTION OF THE DISCLOSURE

The present disclosure is generally related to vascular endothelial growth factor (VEGF)-sequestering hydrogel microspheres with a tunable degradation rate and functionalized with vascular endothelial growth factor receptor 2 (VEGFR2)-mimicking peptides for selectively sequestering unwanted VEGF from blood products. In one particular embodiment, the microspheres bind VEGF as part of an intra-operative process such that VEGF can be removed from the blood products before the products are to be used in a clinical procedure.

In one particular aspect, the present disclosure relates to a method of reducing vascular endothelial growth factor (VEGF) in a blood product of a subject in need thereof. The method comprises contacting a VEGF-sequestering hydrogel microsphere with the blood product, the VEGF-sequestering hydrogel microsphere comprising a polymeric microsphere covalently linked to a VEGF-binding peptide variant derived from vascular endothelial growth factor receptor 2 (VEGFR2).

In another aspect, the present disclosure relates to a method of administering a blood product having reduced vascular endothelial growth factor (VEGF) to a subject in need thereof. The method comprises: preparing a blood product; contacting a VEGF-sequestering hydrogel microsphere with the blood product to reduce VEGF in the blood product, the VEGF-sequestering hydrogel microsphere comprising a polymeric microsphere covalently linked to a VEGF-binding peptide variant derived from vascular endothelial growth factor receptor 2 (VEGFR2); and administering the blood product with reduced VEGF to the subject.

In yet another aspect, the present disclosure relates to a method of treating a disorder exhibiting aberrant angiogenesis in a subject in need thereof. The method comprises administering a VEGF-sequestering hydrogel microsphere comprising a polymeric microsphere covalently linked to a VEGF-binding peptide variant derived from vascular endothelial growth factor receptor 2 (VEGFR2) to the subject.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A depicts the chemical structures of PEG-DT, PEG-M-DT, and PEG-T-DT. The molecular weight of each PEG chain is 3.4 kDa, thus the number of repeat ethylene glycol units, 'n', in each schematic is approximately 77. FIG. 1B is a schematic of VBP microspheres crosslinked with fast-degrading PEG-T-DT crosslinker (F-Type), slow-degrading PEG-M-DT crosslinker (S-Type), and non-degrading PEG-DT (N-Type). FIG. 1C contains phase contrast images (scale bar represents 50 μm) of Trypan-stained Blank F-Type microspheres at day 0 (F-Blank d0) and day 1 (F-Blank d1), S-Type microspheres at day 0 (S-Blank d0) and day 16 (S-Blank d16), and N-Type microspheres at day 0 (N-Blank d0) and day 18 (N-Blank d18). FIG. 1D is a line graph representing mean microsphere area (μm²) over time for F-Blank, S-Blank, and N-Blank microspheres. Peptide-containing microspheres are represented for F-VBP microspheres and S-Scramble microspheres. F-Scramble, S-VBP, N-VBP, and N-Scramble were omitted for brevity, as the degradation profiles for microspheres of each crosslinker type were independent of the presence of peptide.

FIG. 2A depicts sequestered VEGF (ng VEGF per mg microspheres) to microspheres containing peptide (VBP, Scramble) or no peptide (Blank) and varying crosslinker identities (PEG-M-DT, PEG-T-DT, and PEG-DT). Two-way analysis of variance was performed (Microsphere peptide identity p-value<0.0001, microsphere crosslink type p-value<0.0001, interaction p-value>0.05) with post-hoc Student's t-test. Statistical significance relative to Scramble (**) and Blank (*) microspheres for each crosslinker type and relative to both N-VBP and F-VBP is denoted for α=0.05. FIG. 2B depicts VEGF release curves presented as fractional cumulative VEGF release (normalized to the final time point). FIGS. 2A & 2B: Data represent mean+/− standard deviation for three replicates per condition.

FIG. 4A is a schematic of VEGF sequestering by VBP microspheres in HUVEC culture containing 10 ng/mL supplemented VEGF. FIG. 4B depicts relative HUVEC metabolic activity (given as normalized fluorescence intensity of each condition relative to the Blank microsphere condition of each crosslinker type) upon addition of VEGF-containing medium to Blank microspheres (containing no peptide), VBP, or Scramble and varying crosslinker identity. Two-way analysis of variance was performed (microsphere peptide identity p-value<0.0001, microsphere crosslink type p-value>0.05, interaction p-value>0.05) with post-hoc Student's t-test. Statistical significance is denoted compared to Scramble (**) and Blank (*) microspheres at each respective crosslinker type or between conditions in brackets for p-value <0.05 using Student's t-test. Error bars represent the standard deviation about the mean for six replicates per condition. FIG. 4C depicts the amount of phosphorylated VEGFR2 (in ng) measured via ELISA normalized to the total protein content of the cell lysate (in mg) after treatment of HUVECs with microspheres (F-VBP, N-VBP, or N-Scramble) incubated with 10 nmg/mL VEGF in 2 vol. % fetal bovine serum (FBS) in medium 199 for 2 days. Data is presented as mean+/− standard deviation for three replicates per condition, and statistical significance is denoted relative to N-Scramble control at p-value <0.05 (*).

FIG. 5A depicts HUVEC metabolic activity (in fluorescence intensity) in the presence of varying concentrations of VEGF. No VEGF condition is shown as 0.001 ng/mL on x-axis. Statistical significance compared to no VEGF condition denoted with (*) at p-value <0.05 using Student's t-test. FIG. 5B depicts HUVEC metabolic activity (in fluorescence intensity) in the presence of VBP, Scramble, or Blank microspheres crosslinked with PEG-T-DT, PEG-M-DT, or PEG-DT. HUVEC metabolic activity in the absence of microspheres or VEGF is shown as dashed line. Two-way analysis of variance was performed (microsphere peptide identity p-value>0.05, microsphere crosslink type p-value>0.05, interaction p-value>0.05). No statistical differences were observed in post-hoc Bonferroni test.

FIG. 6A is a schematic of the hypothesized impact of VEGF release from VBP microspheres relative to VEGF release from Scramble or Blank microspheres in HUVEC culture. FIG. 6B depicts relative HUVEC metabolic activity (given as normalized fluorescence intensity of each condition relative to the Blank microsphere condition of each crosslinker type) upon addition of Blank, VBP, or Scramble microspheres (with different crosslinker identity) that were pre-incubated in 10 ng/mL VEGF, briefly washed, and delivered to HUVEC culture. Two-way analysis of variance was performed (microsphere peptide identity p-value<0.0001, microsphere crosslink type p-value<0.0001, interaction p-value<0.0001) with post-hoc Student's t-test. Statistical significance is denoted compared to Scramble (**) and Blank (*) microspheres at each respective crosslinker type or between conditions in brackets at p-value <0.05 using Student's t-test. Data represent mean+/− standard deviation for six replicates per condition. FIG. 6C depicts the amount of phosphorylated VEGFR2 (in ng) measured via ELISA normalized to the total protein content of the cell lysate (in mg) after treatment of HUVECs with VEGF releasate from microspheres (F-VBP, N-VBP, or N-Scramble) after pre-loading microspheres with 10 ng/mL VEGF, briefly washing, and incubating microspheres in medium containing 2 vol. % FBS in medium 199 for 3 days. Data is presented as mean+/−standard deviation for three replicates per condition, and statistical significance is denoted relative to N-Scramble control (*) or F-VBP (**) at p-value <0.05 (*) using one-way ANOVA with Tukey's post-hoc test.

FIG. 7A is a schematic demonstrating iPSC-EC sprouting away from cell-dense sphere into surrounding synthetic hydrogel with encapsulated VBP microspheres. FIG. 7B depicts iPSC-EC sprouting quantified as the number of invading Calcein+ cells for each condition. Condition with no microspheres (−μspheres) in the presence of VEGF-containing medium is shown with a dashed line. Two-way analysis of variance was performed (microsphere peptide identity p-value>0.05, microsphere crosslink type p-value=0.002, interaction p-value=0.016) with post-hoc Student's t-test. Statistical significance for Student's t-test denoted compared to Scramble (**) and no microsphere (*) conditions or between conditions in brackets at α=0.05). Data is presented as mean+/−standard deviation for eight replicates per condition.

FIG. 8A is a schematic of laser ablation of the mouse choroid in murine CNV model. Laser ablation was performed at the 3-, 9-, and 12-o'clock positions on the posterior of the eye. FIG. 8B are representative fluorescent micrographs of ICAM2+ vessels in mouse CNV model after treatment with N-Scramble, F-Scramble, N-VBP, or F-VBP microspheres, or sham (saline) or Soluble VBP. FIG. 8C depicts mean CNV area in μm² (defined as the area of ICAM2+ vasculature in the choroid) after treatment with either N-Scramble (N-Scr), F-Scramble (F-Scr), N-VBP, or F-VBP microspheres. Data were aggregated for two independent experiments, and error bars represent standard error about the mean (SEM) for 6 (N-Scramble), 5 (F-Scramble), 7 (N-VBP), and 14 mice (F-VBP). Statistical significance was determined using one-way analysis of variance with Tukey's post-hoc test and a Tukey multiple comparisons correction and is denoted for p-value <0.05 relative to N-Scramble (**) or F-Scramble (*) microspheres. FIG. 8D depicts mean CNV area ($\mu m^2$) after treatment with saline (Sham), 20 μg/mL Soluble Scramble, or 20 μg/mL Soluble VBP. Error bars represent SEM for 8 mice per condition. Statistical significance was determined using one-way analysis of variance with Tukey's post-hoc test and Tukey multiple comparisons correction and is denoted (*) for p-value <0.05 relative to Sham.

FIG. 12A is a schematic of platelet activation and subsequent VEGF sequestering to VBP microspheres incubated in PC. FIG. 12B depicts multiplexed bead-based ELISA performed to assess the abundance of 12 pro-angiogenic growth factors in the supernatant after incubation of microspheres with PC. Data was compared to standard curve generated using recombinant growth factors in PBS, and the abundance of each growth factor in supernatant was calculated from the standard curve using 4-PL analysis in GraphPad Prism. ND=Not Detected. Statistical comparisons were made using one-way ANOVA with Fisher's least significant difference post-hoc test. Statistical significance is denoted for p-value <0.05 (*) between the conditions indicated in brackets. FIG. 12C depicts the quantification of VEGF sequestering to VBP microspheres (in % bound VEGF) calculated by subtracting the concentration of VEGF in the no microsphere control (NS) by the concentration of VEGF in each respective microsphere condition and dividing by the total amount of VEGF in the NS control. Statistical comparisons were made using one-way ANOVA and Bonferroni post-hoc test and is denoted for p-value<0.05 relative to Scramble (**) and Blank (*) microspheres. FIG. 12D depicts VEGF sequestering to linear dimeric VBP, $VBP_2$, and dimeric Scramble, $Scr_2$, at varying peptide concentrations (presented as % peptide per norbornene group during microsphere synthesis with PEG-NB). % Bound VEGF was calculated as described above. Statistical analysis was performed using two-way ANOVA (peptide identity, peptide concentration, and interaction p-value <0.05) with post-hoc Bonferroni test denoted for p-value <0.05 with an asterisk (*) comparing $VBP_2$ and $Scr_2$ at each peptide concentration.

FIG. 13A depicts quantification of EdU+/Hoechst+ HUVEC nuclei, denoted as the fraction of HUVECs in S-phase, in the no VEGF control (−) and in the presence of microspheres either pre-incubated in PBS or pre-incubated in PC. Statistical analysis was performed relative to Blank and Scramble control microspheres in either PBS or PC. Statistical significance among each group (PBS or PC) was performed using one-way ANOVA with post-hoc Dunnett test and is denoted for p-value<0.05 compared to Scramble (**) and Blank (*) microspheres. Alternatively, statistical analysis was performed relative to each respective microsphere condition incubated in PC or PBS using two-way ANOVA, and statistical significance is denoted for p-value<0.05 (*). FIG. 13B is a schematic demonstrating the hypothesized mechanism whereby microspheres incubated in PC took up PC-derived proteins and GFs via mass transport.

FIG. 18A is a phase contrast image of glass capillary used for injection in choroidal neovascularization model. Image analysis (NIS Elements) revealed that the mean diameter of the capillary tube is ~6 μm at the tip. FIG. 18B is a phase contrast image of sonicated N-Blank microspheres stained with Trypan blue. FIG. 18C depicts histograms of microsphere diameter after emulsifying via vortexing for 60 seconds or sonication at one of three different power levels for 40 seconds. Dashed line indicates 6 μm diameter of capillary tube. FIG. 18D depicts the mean diameter of N-Blank microspheres generated (as shown in FIG. 18C). Microsphere diameter was strongly influenced by the emulsion conditions (one-way ANOVA p-value <0.0001), and the microspheres generated via sonication at 100 W exhibited the smallest mean diameter relative to all other conditions (p-value <0.0001 via ANOVA and Tukey's post-hoc test). Dashed line indicates 6 μm diameter of capillary tube.

DETAILED DESCRIPTION

Figure 1A:
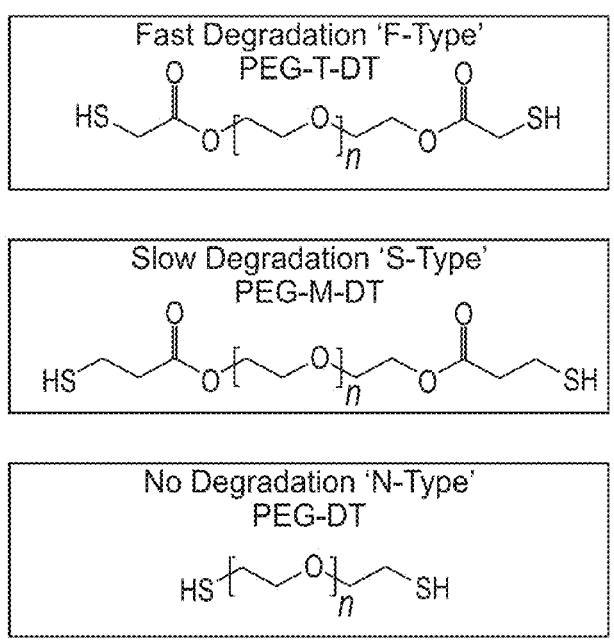
FIGS. 1A-1D depict the influence of chemical crosslinker identity on PEG microsphere degradation rate.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Growth factor regulation is a key function of the extracellular matrix (ECM) and is particularly important for proper blood vessel growth and maturation during wound healing. Blood vessel sprouting associated with angiogenesis is required for effective healing, and it is highly dependent on the ECM to regulate growth factor (GF) activity via sequestering, spatial patterning, and cell-demanded release. One particularly well characterized example involves regulation of vascular endothelial growth factor (VEGF) activity. VEGF is an important factor during angiogenesis, and previous investigations have demonstrated blood vessel sprouting within a limited VEGF concentration range in vivo. In the native ECM, VEGF activity can be regulated via binding to ECM components, such as heparan sulfate proteoglycans (HSPGs) and fibronectin. In addition, cell-demanded proteolytic degradation (via matrix metalloproteinases) of ECM components can increase unbound VEGF and consequently increase local VEGF activity. The need to maintain VEGF activity in a particular concentration range during angiogenesis has motivated the use of therapeutic interventions to regulate VEGF activity when natural regulation is dysfunctional, such as during diabetic wound healing and tumor growth.

Generally, the present disclosure is directed to the use of hydrogel microspheres for sequestering problematic growth factors, and specifically vascular endothelial growth factor (VEGF), in subjects in need thereof. The hydrogel microspheres are typically prepared as polymeric microspheres covalently linked to varying concentrations of VEGFR2-derived binding peptides with varying serum stability. The polymeric microspheres can be prepared from polymeric materials such as polyethylene glycol (PEG), polyamidoamine, polyglycerol, poly(e-oxazoline), poly(N-isopropylacrylamide), hyaluronic acid, dextran, alginate, gelatin, and combinations thereof. In one particularly suitable embodiment, the polymeric microsphere is composed of PEG. It has been found that the presence of the tethered VEGF-derived binding peptides (also referred to herein as VEGF-binding peptides (VBPs)) can significantly control VEGF availability and VEGF-dependent endothelial cell behavior in vitro and angiogenesis in vivo.

Microspheres containing VBPs were prepared using thiol-ene chemistry by emulsifying and UV-crosslinking a solution containing VBP, dithiol crosslinker, multi-arm norbornene-functionalized PEG, and photoinitiator. Four-arm or eight-arm poly(ethylene-glycol) (PEG; Mn=20,000; Jenkem) may be functionalized with norbornene moieties at each arm to generate PEG-norbornene (PEG-NB) in order to utilize thiol-ene photopolymerization. More particularly, four-arm or eight-arm PEG, terminated at each arm with a hydroxyl functional group, is reacted under constant stirring in a flask, purged with argon during dissolution and reaction, with 10 molar equivalents (with respect to the number of PEG arms) of 5-norbornene-2-carboxylic acid (Sigma-Aldrich) in dichloromethane (Fisher), five molar equivalents of N,N'-dicyclohexylcarbodiimide (Sigma), half molar equivalent of 4-dimethylaminopyridine (Sigma-Aldrich), and five molar equivalents of pyridine (Sigma-Aldrich). Derivatization is determined as >90% using 1H nuclear magnetic resonance by comparing the chemical shift expected for ether bonds associated with PEG (~3.4 ppm) with the chemical shift expected for the norbornene group (~5.8-6.2 ppm).

PEG microspheres are then synthesized using a water-in-water emulsion. Microspheres containing covalently immobilized VBPs may be synthesized using an aqueous emulsion of two phases, a PEG-rich discontinuous phase and a dextran-rich continuous phase. In the PEG-rich phase, PEG-NB is mixed with a half molar equivalent of PEG3400 dithiol (Laysan Bio) along with a peptide solution for the particular VBP. Peptide solutions for the various VBPs, as described below, are mixed into the PEG-rich phase. To form the microspheres, the PEG-dextran mixture is vortexed and photopolymerized under ultraviolet light. To form microspheres of a smaller diameter, the PEG-dextran mixture is sonicated using a probe sonicator and photopolymerized under ultraviolet light.

The microspheres formed using the above procedure exhibited a mean diameter of approximately 5 μm to 10 μm, including approximately 8 μm to 10 μm (see FIGS. 18A-18D). For microsphere injections, a mean diameter of 5 μm or less is necessary and requires probe sonication to generate microspheres of a smaller diameter. Sonicated microspheres exhibited a mean diameter of 5 μm.

VEGF binding peptides are synthesized using standard Fmoc solid phase peptide synthesis. The peptides are amidated at the carboxy terminus by synthesizing on MBHA Rink Amide resin (EMD Novabiochem). Particularly, VEGF binding peptides used with the hydrogel microspheres are listed in Table 1.

be treated with the blood products once problematic growth factors (i.e., VEGF) have been removed.

In particular embodiments, the methods of the present disclosure further include preparing the blood products, for example, the platelet lysates by centrifuging platelets and separating the plasma component (consisting of the supernatant). Platelets may then be resuspended in phosphate buffered saline and treated with three freeze/thaw cycles. Platelets are then centrifuged and the supernatant collected, sterile filtered, and used in subsequent studies as "platelet concentrate." In a subset of studies, the platelets with plasma are freeze/thawed and incubated directly with microspheres as described below.

Microspheres containing VBPs may be incubated at 1 mg/mL with platelet concentrate for 4 h at 37° C. on a lab rotator. Alternatively, microspheres containing VBPs may be incubated at 1 mg/mL with activated platelets with plasma for 4 h at 37° C.

Generally, the methods of using the VEGF-sequestering hydrogel microspheres enable improved selective removal and reduction of VEGF from blood products, particularly in autologous blood products, as compared to previous antibody-based approaches that provide limited binding capacity, high cost and inconvenient/ineffective clinical procedures. As used herein, "VEGF-sequestering hydrogel microspheres" refer to hydrogel microspheres linked to a VEGF-binding peptide (VBP) that specifically binds to VEGF. Particularly, while anti-VEGF antibodies and other soluble antagonists have been used to reduce excess levels of growth factor, these treatments can readily diffuse away

TABLE 1

VEGF Binding Peptides (VBP)

| Sequence Abbreviation | Sequence | SEQ ID NO. |
|---|---|---|
| VBP | CE{$F_d$}{$A_d$}{$Y_d$}{$L_d$}IDFNWEYPASK | 1 |
| VBP$_{WT}$ | CELNVGIDFNWEYPASK | 2 |
| Scramble | CD{$A_d$}PYN{$F_d$}EFAWE{$Y_d$}IS{$L_d$K} | 3 |
| VBP$_{2,a}$ | (E{$F_d$}{$A_d$}{$Y_d$}{$L_d$}IDFNWEYPASK)$_2$KC | 4 |
| VBP$_{2,b}$ | (E{$F_d$}{$A_d$}{$Y_d$}{$L_d$}IDFNWEYPAS)$_2$KKKC | 5 |
| Scramble$_{2,b}$ | (D{$A_d$}PYN{$F_d$}EFAWK{$Y_d$}{$L_d$}E)$_2$KC | 6 |
| VBP$_{2,c}$ | (E{$F_d$}{$A_d$}{$Y_d$}{$L_d$}IDFNWEYPAS)$_2$KC | 7 |
| VBP$_{2,\ linear}$ | KE{$F_d$}{$A_d$}{$Y_d$}{$L_d$}IDFNWEYPASKCKSAP YEWNFDI{$L_d$}{$Y_d$}{Ad}{$F_d$}EK | 8 |
| Scramble$_{2,linear}$ | KD{$A_d$}PYN{$F_d$}EFAWE{$Y_d$}IS{$L_d$}KCK{$L_d$}S {$Y_d$}EWAFE{$F_d$}NYP{$A_d$}DK | 9 |
| VBP$_{2,PEG27}$ | C{βA}K({βA}PEG-27) KSAPYEWNFD{$L_d$}{$Y_d$}{$A_d$}{$F_d$}E)$_2$ | 10 |
| | CRGDS | 11 |
| | KCGGPQGIWGQGCK | 12 |

The hydrogel microspheres can be contacted with solutions, and in particular blood products. Suitable blood products include platelet-rich plasma (PRP), platelet lysates, and combinations thereof. In particularly suitable embodiments, the blood products are autologous blood products; that is the blood products are obtained from the same subject that will from the injection site, which is problematic for at least two reasons. First, the effectiveness of a given dose diminishes over time as the therapeutic molecules diffuse away from the site of interest, and, second, the molecules that diffuse away from the site of interest are often still biologically active and can cause undesirable side effects elsewhere in the body.

As used herein, "reduce", "reducing", "modulate", and/or "modulating" interchangeably refer to lowering the level or concentration of a growth factor (e.g., VEGF) in a blood product as compared to the level or concentration of the growth factor in the blood product prior to being contacted with the hydrogel microspheres of the present disclosure.

In some aspects of the present disclosure, the methods of use are desired to treat a subject in need thereof. As such, a subject in need thereof, as it relates to the therapeutic uses herein, is one identified to require or desire medical intervention. More particularly, the methods of the present disclosure are to be used with a subset of subjects who are suspected of having and/or have angiogenesis-mediated disease, disorder or condition, and in particular, a disease, disorder or condition selected from disorders exhibiting aberrant angiogenesis, including choroidal neovascularization, age-related macular degeneration, acavernous hemangioma formation, tumor growth, hereditary hemorrhagic telangiectasia, psoriasis, diabetic retinopathy or retinopathy of prematurity (ROP). In other aspects, the methods are used to treat subjects experiencing angiogenesis-related conditions such as diabetic wound healing, tumor growth, and/or hemangioma formation. Subjects may be susceptible to or at elevated risk for angiogenesis-mediated diseases or disorders (e.g., choroidal neovascularization) and the like due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for angiogenesis-mediated disease or disorder.

Various functions and advantages of these and other embodiments of the present disclosure will be more fully understood from the examples described below. The following examples are intended to illustrate the benefits of the present disclosure, but do not exemplify the full scope of the disclosure.

EXAMPLES

Example 1

In this Example, VEGF-sequestering hydrogel microspheres used in the present disclosure were prepared and analyzed for their regulation of VEGF activity in vitro and in vivo.

Materials and Methods

Peptide Synthesis and Characterization

Peptides were synthesized and characterized as described in Belair et al., Biomacromolecules. 15 (2014) 2038-2048. VEGF-binding peptide (VBP) (SEQ ID NO:1) and a peptide with the same composition as VBP, but with a scrambled sequence (Scramble) (SEQ ID NO:3) were synthesized using fmoc solid phase peptide synthesis on an automated microwave peptide synthesizer (Discover; CEM) equipped with automated liquid handling (Liberty1; CEM). All amino acids and Rink Amide MBHA resin were purchased from EMD Novabiochem. Resin was initially swelled in N,N-dimethylformamide (DMF; Fisher) for 10 minutes and subsequently deprotected in 20 vol. % piperidine (Sigma), 80 vol. % DMF, and 0.1M HOBt (Advanced Chem Tech) for 5 minutes under microwave at 70° C. Resin was washed twice in DMF before coupling, and the reaction vessel was subsequently filled with four molar equivalents of amino acid (dissolved at 0.2M in DMF) with respect to free amines, four equivalents of HBTU (Advanced Chem Tech), and eight equivalents of diisopropylethylamine (DIPEA; Fisher), which was dissolved at 35 vol. % in N-methyl-2-pyrrolidone (Fisher). Coupling for all amino acids was performed at 70° C. (except for cysteine, which was coupled at 50° C.) for 5 minutes under microwave. Peptide purity was verified using reverse phase high performance liquid chromatography (Shimadzu $C_{18}$ column) Peptide identity was verified using time-of-flight mass spectroscopy (MALDI-ToF; Bruker), and peptide content was determined using an Ellman's assay (Thermo Scientific) to measure free thiols.

PEG Derivatization with Norbornene

Poly(ethylene glycol) (PEG; Mn=20,000; Jenkem) with four or eight arms was derivatized with norbornene groups on each arm. Briefly, N,N'-Dicyclohexylcarbodiimide (2.1 g) and 5-norbornene-2-carboxylic acid (2.5 ml) were added to a round bottom flask and dissolved in 30 ml of anhydrous dichloromethane (DCM). The head space was then purged with dry argon and the solution was allowed to stir for 20 minutes.

In a second flask, 10 g of 4-arm PEG (20 k MW from Jenkem Technology) and 120 mg of 4-(dimethylamino) pyridine were dissolved in 40 ml of anhydrous DCM containing 0.8 ml of pyridine. Next, the PEG solution was transferred into the first flask using a syringe. The reaction was allowed to proceed at room temperature for two hours.

The reaction mixture was passed through a fritted Buchner funnel (medium) to remove suspended urea salts that formed during the reaction. The filtrate was then precipitated using 900 ml of cold diethyl ether, and the solids were collected on qualitative grade filter paper. Vacuum was pulled on the sample until a dense cake was formed. Following drying, the reaction product was dissolved in 90 ml of chloroform and extracted twice using 50 mM glycine buffer solution (pH 10) in order to remove residual norbornene acid. Residual water in the chloroform phase was then extracted using a saturated sodium chloride solution. Finally, the chloroform fraction was added to 900 ml of cold diethyl ether in order to precipitate the purified PEG norbornene, which was then collected and dried on filter paper using vacuum filtration.

All reagents here were purchased from Sigma-Aldrich. Four-arm and eight-arm PEG functionalization with norbornene was verified with 1H nuclear magnetic resonance as described in Fairbanks et al., Adv. Mater. 21 (2009) 5005-5010.

Synthesis of Ester-Containing PEG Dithiol Molecules

PEG-diester dithiol molecules were synthesized through the reaction of hydroxy-terminated PEG (Mn=3,400; Spectrum) with thiol-containing molecules, 3-mercaptopropionic acid (MP Biomedicals) or thioglycolic acid (MP Biomedicals). PEG derivatized with 3-mercaptopropionic acid is hereafter referred to as PEG-M-DT, and PEG derivatized with thioglycolic acid is hereafter referred to as PEG-T-DT. PEG was dried via reflux in toluene under argon gas, and subsequently 3-mercaptopropionic acid or thioglycolic acid was added to PEG (10 gram basis) at 20 molar equivalents relative to PEG hydroxyl groups. Reagents were mixed in a round-bottom flask with a p-toluenesulfonic acid catalyst (0.4 mmole; Sigma) and dithiothreitol (0.1 mmole; Sigma) reducing agent. The mixture was refluxed overnight using a Dean-Stark apparatus to remove water produced in the reaction. The contents of the flask were then transferred to a RotoVap to remove the toluene. The final product was precipitated in ice-cold acetone and vacuum filtered. The diester dithiol products were dried overnight under vacuum and stored at −20° C. The reaction proceeded to >95% completion as verified using $_1$H nuclear magnetic resonance (CDCl$_3$), and thiol content was verified using an Ellman's assay.

Generation of PEG-Norbornene Microspheres

PEG-norbornene microspheres were generated through a thiol-ene reaction between PEG-norbornene and either PEG-T-DT, PEG-M-DT, or PEG dithiol (PEG-DT; Mn=3, 400; Laysan Bio). The reaction consisted of an aqueous emulsion between a PEG-rich dispersed phase and a Dextran-rich continuous phase. The PEG-rich phase contained 20 wt. % of four-arm or eight-arm PEG-norbornene, 0.5 molar equivalents of thiol crosslinker (PEG-T-DT, PEG-M-DT, PEG-DT) relative to PEG arms, 0.016 molar equivalents of peptide (VBP or Scramble), and a final concentration of 0.05 wt. % photoinitiator (Irgacure 2959) in deionized (DI) water. A blank condition was also prepared, using an equivalent amount of DI water in place of the peptide solution. All components of the PEG-rich phase were combined and purged with nitrogen prior to the addition of a 6-fold volumetric excess (relative to PEG phase) of Dextran-rich phase, consisting of 40 wt. % Dextran (Mn=40,000; Alfa Aesar) in KCl buffer. The PEG-rich phase was emulsified via vortexing for one minute in the Dextran phase, and the emulsion was allowed to stabilize for 20 minutes before being exposed to UV light (1.1 J/cm$^2$) to initiate the polymerization reaction. Impurities and unreacted reagents were removed with a 25-fold dilution in DI water followed by centrifugation at 1600×g for 5 minutes and two subsequent washes in DI water. The final product was then suspended in DI water, frozen in liquid nitrogen, and lyophilized Peptide-containing microspheres were suspended in phosphate buffered saline (PBS; Fisher Scientific), and peptide content was verified using either Micro-BCA assay (Thermo Scientific) or by UV-Vis absorbance at 260 nm corresponding to absorbance of tryptophan.

The constraint of microsphere diameter imposed by the capillary tube (6 μm) for injection in the mouse choroidal neovascularization model required the generation of microspheres <6 μm in diameter. Microspheres suitable for injection (<5 μm) in the mouse choroidal neovascularization model were generated as above except that emulsification was provided by probe sonication (Branson Sonifier 250) for 40 seconds at 100% duty, and UV polymerization was performed immediately without a stabilization period. Microspheres were washed and characterized as described above. The mean diameter of microspheres was highly dependent on the emulsion conditions (one-way ANOVA p-value <0.0001), and microspheres generated via sonication (~5 μm) exhibited a smaller diameter than microspheres generated via vortexing (~8 μm) (FIGS. 18A-18D).

Characterization of Microsphere Degradation Rate

Microsphere conditions were suspended at 1 mg/mL in PBS and rotated at 37° C. Each day, 10 μL of each microsphere suspension was placed on a microscope slide with 10 μL Trypan Blue (Sigma) stain. Microspheres were then imaged using phase contrast microscopy (Nikon TE300 equipped with 10× objective), and mean microsphere diameter was characterized using ImageJ. This procedure was repeated daily until degradable microspheres (crosslinked with PEG-T-DT and PEG-M-DT) were completely degraded.

Figure 1B:
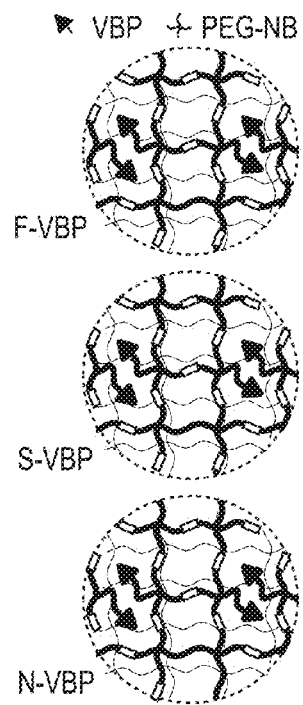
Figure 1C:
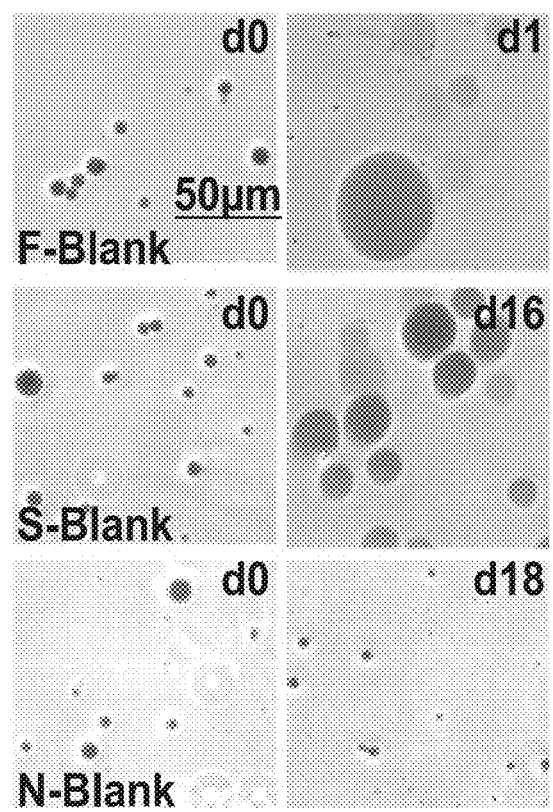
Figure 1D:
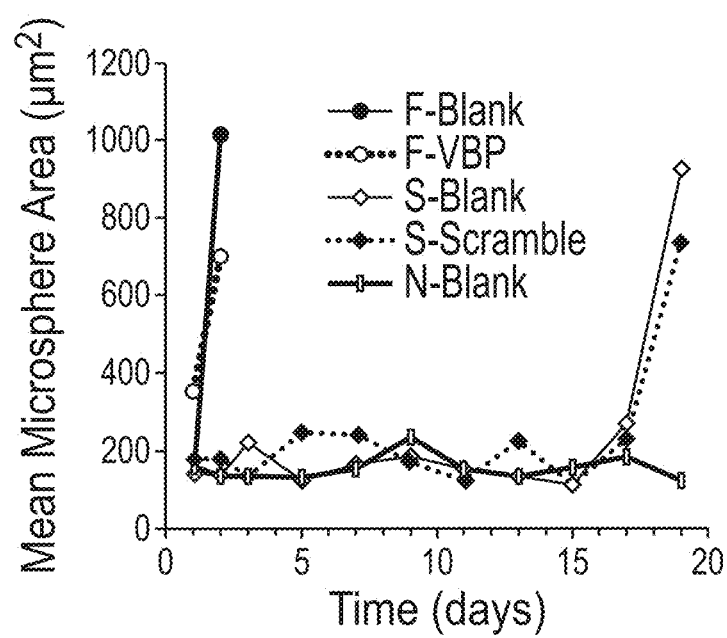
Figure 2A:
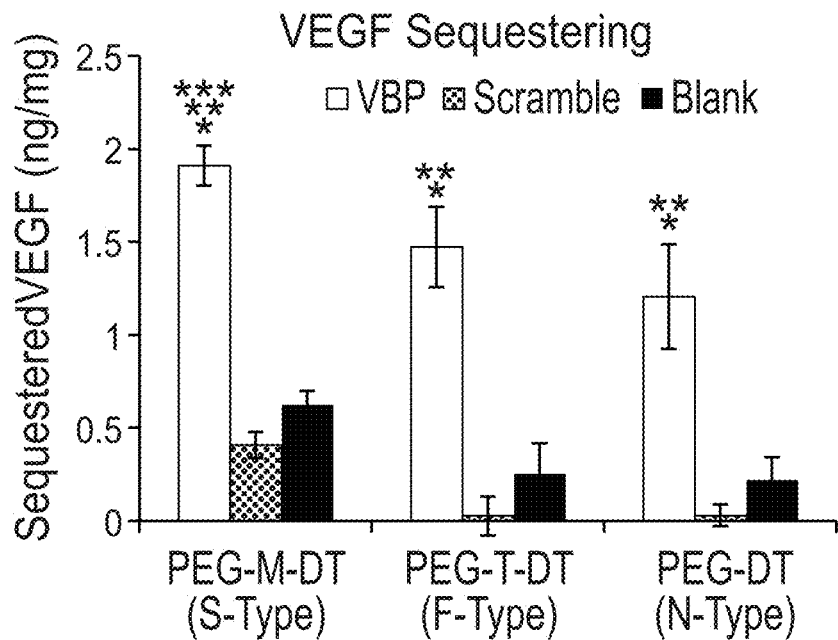
FIGS. 2A & 2B depict that VBP microspheres sequestered VEGF, and VEGF release rate was dependent on crosslinker identity.
Figure 2B:
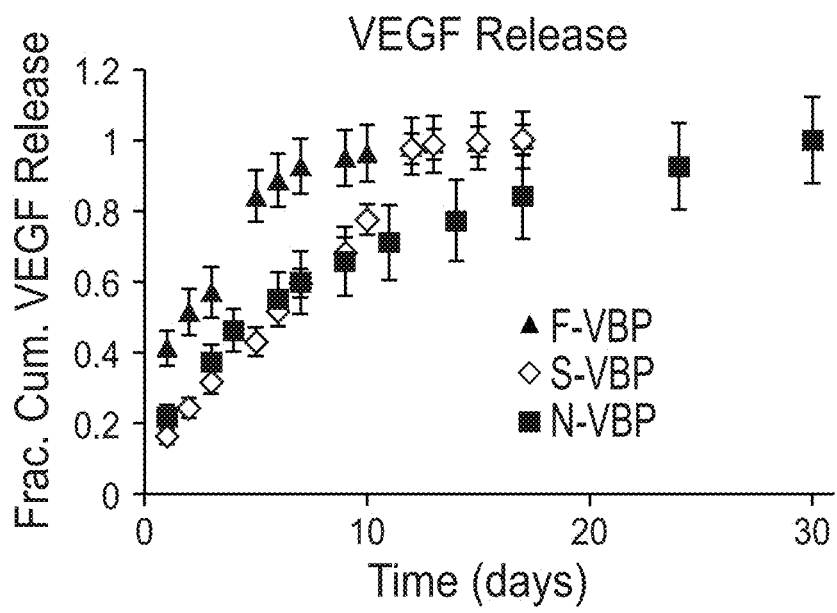
Figure 3A:
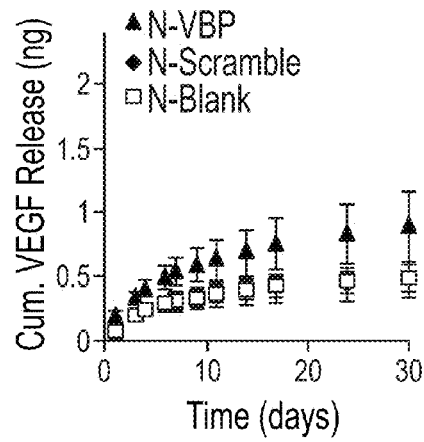
FIGS. 3A-3C depict cumulative VEGF release (ng) from Blank, VBP, or Scramble microspheres (crosslinked with PEG-T-DT, PEG-M-DT, or PEG-DT) pre-loaded with VEGF. Error bars were propagated at each time point and represent one standard deviation about the mean cumulative release for each time point for three replicates per condition.
Figure 3B:
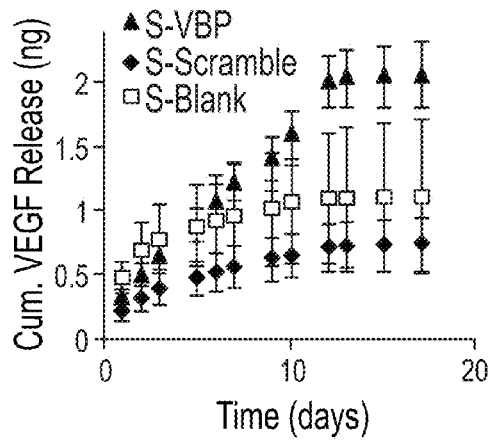
Figure 3C:
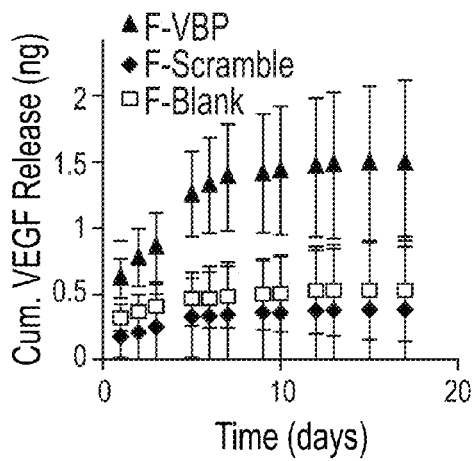

Microspheres crosslinked with ester-containing, dithiol terminated crosslinking groups (FIGS. 1A & 1B) exhibited degradation rates that were variable based on the presence and proximity of ester bonds to terminal thiol groups (FIGS. 1C & 1D). Microspheres crosslinked with PEG-T-DT are referred to herein as F-type microspheres (Fast-degrading), with PEG-M-DT as S-type microspheres (Slowly-degrading), and with PEG-DT as N-type microspheres (Non-degrading). N-type microspheres with no peptide (N-Blank) maintained a constant mean diameter over 18 days (FIG. 1C N-Blank & FIG. 1D). In contrast, S-type microspheres containing no peptide (S-Blank) or containing Scramble peptide (S-Scramble) both exhibited a sharp increase in mean microsphere diameter at day 16 (FIG. 1C S-Blank) and were completely degraded in PBS after 18 days (FIG. 1D) or in protein-containing buffer after 12 days (FIG. 2B). F-type microspheres containing no peptide (F-Blank) or containing VBP (F-VBP) both exhibited a sharp increase in mean microsphere diameter at day 1 (FIG. 1C F-Blank) and were completely degraded in PBS after 3 days (FIG. 1D) or in protein-containing buffer after 5 days (FIG. 2B).

Influence of Microsphere Degradation Rate on VEGF Sequestering and Release

Microspheres were assayed for VEGF sequestering and release. VEGF binding was assessed by incubating microspheres in 10 ng/mL VEGF because of the similar in vivo VEGF abundance in wound exudate (~10 ng/mL) and platelet releasate (~1-10 ng/mL). For VEGF sequestering studies, microspheres were incubated in 0.1 wt. % bovine serum albumin (BSA; Fisher) in PBS with 9.9 ng/mL of human recombinant VEGF165 (R&D Systems), hereafter referred to as VEGF, and 0.1 ng/mL of [$^{125}$I]VEGF (Perkin Elmer) for 4 hours at 37° C. Microspheres were subsequently centrifuged at 10,600×g for 5 minutes, and the supernatant counts per minute (CPM) were measured with a gamma counter (Perkin Elmer) and correlated to VEGF concentration using a standard curve. For release studies, microspheres were pre-loaded with VEGF as above and were incubated in 0.1 wt. % BSA in PBS after washing out un-sequestered VEGF. Microspheres were centrifuged as above, and the supernatants at the specified time points in FIG. 2B and FIGS. 3A-3C were measured on gamma counter and correlated to released VEGF at each time point. VEGF release was measured until the CPM at a given time point was indistinguishable from background.

VBP microspheres sequestered VEGF independent of crosslinker identity, and microsphere degradation rate influenced the release rate of sequestered VEGF. VBP microspheres sequestered significantly more VEGF than Blank and Scramble microspheres regardless of crosslinker identity (FIG. 2A). S-VBP microspheres sequestered significantly more VEGF than either N-VBP or F-VBP microspheres (FIG. 2A), though the interaction between crosslinker and peptide identity was not statistically significant via ANOVA. After VEGF sequestering, VBP microspheres released VEGF at a rate that was proportional to the degradation rate of each respective crosslinker (FIG. 2B). S-VBP microspheres exhibited sustained release similar to N-VBP microspheres until day 12, at which point S-VBP microspheres released VEGF rapidly (FIG. 2B). This result is consistent with microsphere degradation data showing complete degradation of S-Type microspheres after approximately two weeks. F-VBP microspheres exhibited more of a "burst" release profile compared to S-VBP and N-VBP microspheres (FIG. 2B), consistent with the fast degradation rate of F-type microspheres. Importantly, the cumulative amount of VEGF released from VBP microspheres was significantly higher than that from Scramble and Blank microspheres (FIGS. 3A-3C), reflecting the higher amount of VEGF sequestered to VBP microspheres of all three crosslinker types (FIG. 2A) relative to Scramble and Blank microspheres.

Impact of VBP Microsphere Degradation on Signaling and Activity of VEGF in HUVEC Culture Human umbilical vein endothelial cells (HUVEC; Lonza) were expanded in Medium 199 (CellGro) supplemented with EGM2 and penicillin/streptomycin (Gibco) and were used between passages 6-10. On the day before experiments, HUVECs were plated at 4,000 cells/well in medium containing 2% FBS (Gibco) in Medium 199 in black polystyrene plates pre-coated with Gelatin (Sigma). The next day, microsphere conditions were sanitized by suspension in 70 vol. % ethanol (Fisher) in DI water for at least one hour. Microspheres were washed three times in sterile PBS. For VEGF sequestering experiments, sanitized microspheres were suspended at 1 mg/mL in Medium 199 (M199; Cell-Gro) with 2% FBS serum and either 0 or 10 ng/mL VEGF. For VEGF sustained release experiments, sanitized microspheres were suspended in 0.1 wt. % BSA in PBS with 10 ng/mL VEGF for 45 minutes at 37° C. Microspheres were subsequently centrifuged at 10,600×g for 5 minutes, and the supernatant was aspirated. Microspheres were then suspended at 1 mg/mL in Medium 199 with 2% FBS. For both VEGF sequestering and sustained VEGF release experiments, culture medium was aspirated from HUVEC-seeded plates, and microsphere suspensions were added to plate at 100 μL per well. HUVECs were incubated with microspheres at 37° C., 95% relative humidity, and 5% $CO_2$ for 48 hours. At the end of the incubation period, a CellTiter-Blue Cell Viability Assay (Promega) was performed to measure cell metabolic activity by adding 20 μL CellTiter-Blue to each well, incubating for an additional 4 hours, and measuring fluorescence intensity at $590_{excitation}/612_{emission}$. Conditions were assayed in replicates of 6 and compared via two-way analysis of variance (ANOVA) and post-hoc Student's t-test ($\alpha=0.05$), and data are displayed as normalized fluorescence intensity relative to the Blank microsphere condition with each crosslinker type.

Figure 4A:
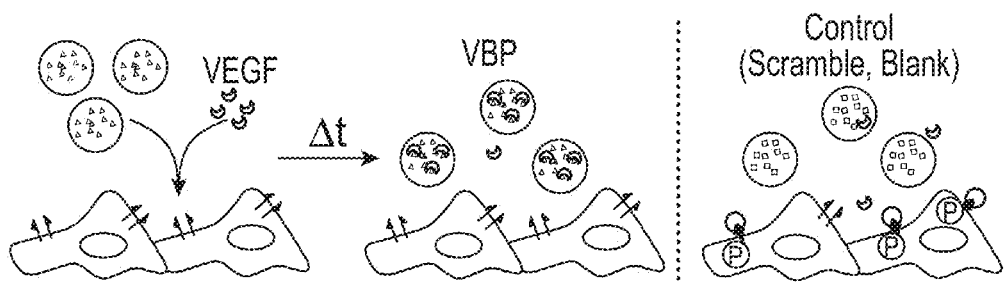
FIGS. 4A-4C show that VBP microspheres reduced VEGF-dependent metabolic activity and VEGFR activation in HUVEC culture.
Figure 4B:
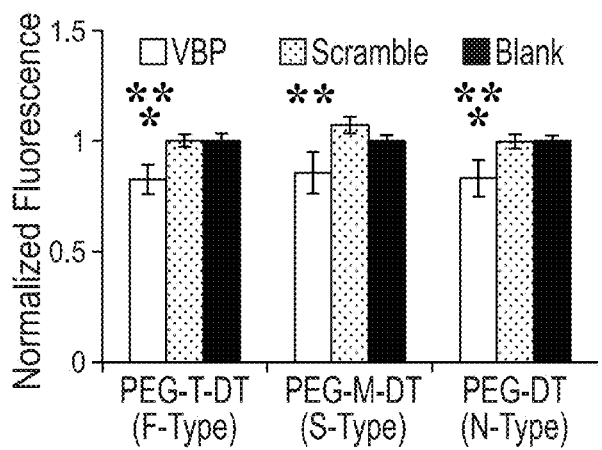
Figure 4C:
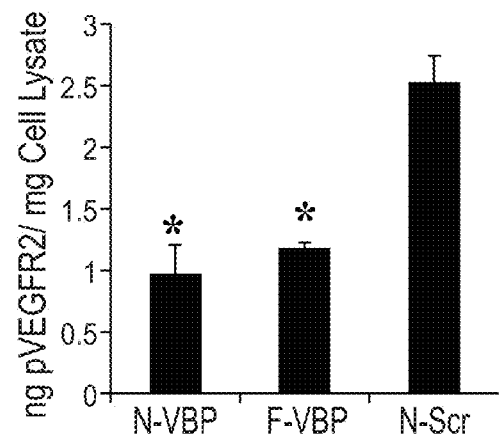
Figure 5A:
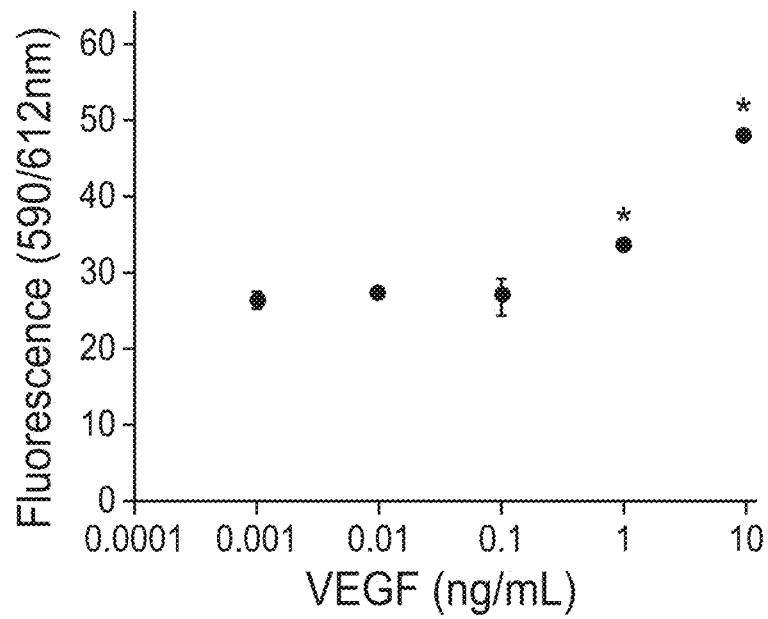
FIGS. 5A & 5B depict HUVEC metabolic activity in the presence of microspheres alone or VEGF alone.
Figure 5B:
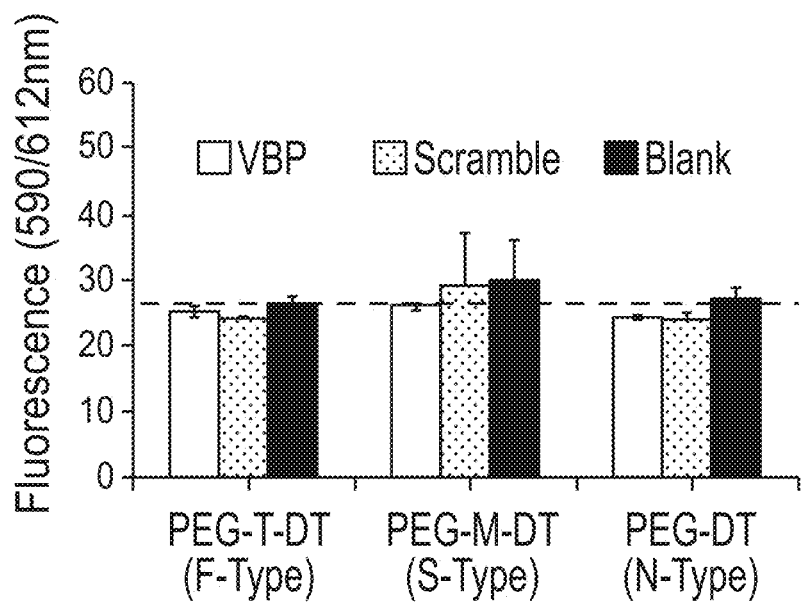
Figure 19:
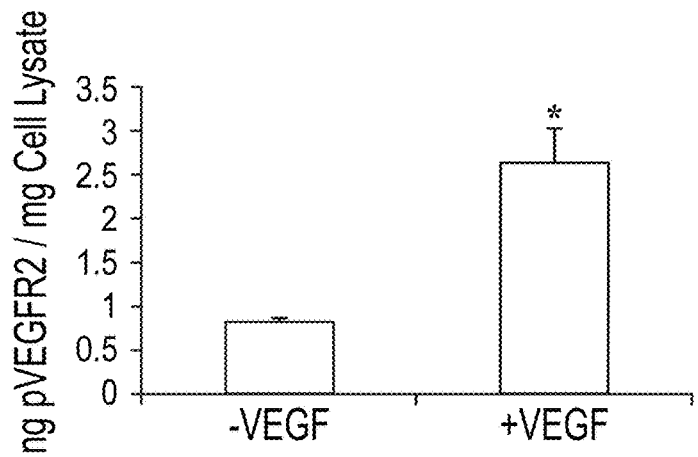
FIG. 19 depicts the amount of phosphorylated VEGFR2 (in ng) measured via ELISA normalized to the total protein content of the cell lysate (in mg) after treatment of HUVECs with medium (2 vol. % FBS in M199) containing no supplemented VEGF or containing 10 ng/mL supplemented VEGF. Data is presented as mean+/−standard deviation for three (−VEGF) or five replicates (+VEGF), and statistical significance is denoted for p-value <0.05 using Student's t-test (*).

VBP microspheres reduced VEGF activity in culture upon VEGF sequestering regardless of crosslinker identity (FIG. 4A). Soluble VEGF in the cell culture medium increased HUVEC metabolic activity at 1 and 10 ng/mL relative to the control without VEGF supplementation (FIG. 5A), and thus 10 ng/mL VEGF was used for sequestering and release experiments in HUVEC metabolic activity assays. Further, 10 ng/mL of supplemented VEGF stimulated VEGFR2 phosphorylation in HUVECs three-fold relative to HUVECs treated with no VEGF (FIG. 19), and given the similar abundance of VEGF in wound exudate (~10 ng/mL) and platelet releasate (~1-10 ng/mL), 10 ng/mL VEGF was used for sequestering and release experiments in HUVEC metabolic activity assays. Regardless of crosslinker identity, VBP microspheres reduced HUVEC metabolic activity in culture medium with soluble VEGF (normalized data shown in FIG. 4B). Specifically, F-VBP, S-VBP, and N-VBP microspheres reduced VEGF-dependent HUVEC metabolic activity relative to F-Scramble, S-Scramble, and N-Scramble microspheres, respectively. No statistical differences were observed between F-VBP, N-VBP, and S-VBP (FIG. 4B), which suggests that the difference in VEGF sequestering between these conditions was not biologically-relevant. Both F-VBP and N-VBP microspheres reduced HUVEC metabolic activity relative to F-Blank and N-Blank microspheres, respectively (FIG. 4B). F-VBP and N-VBP microspheres also reduced the levels of phosphorylated VEGFR2 (pVEGFR2) relative to N-Scramble microspheres in the presence of VEGF (FIG. 4C), which suggests that VBP microspheres reduced VEGF signaling in culture via VEGF sequestering and an effective reduction of soluble VEGF available to HUVECs.

Influence of VEGF Sequestering and Release on VEGF Receptor Phosphorylation

HUVECs were expanded and used between passages 4-6 for VEGFR2 phosphorylation measurements. Prior to addition to HUVECs, the microspheres used in studying VEGF sequestering (F-VBP, N-VBP, and N-Scramble) were sanitized by exposing to UV for 30 minutes and were incubated at 1 mg/mL in M199 supplemented with 2 vol. % FBS and 10 ng/mL VEGF for 2 days at 37° C. Alternatively, microspheres used in studying VEGF release (F-VBP, N-VBP, N-Scramble) were sanitized and were incubated at 1 mg/mL in 0.1 wt. % BSA in PBS supplemented with 10 ng/mL VEGF for 4 hours, centrifuged, washed briefly in 2 vol. % FBS in M199, and incubated in 2 vol. % FBS in M199 for 3 days. On day 0 of experiments, HUVECs were passaged with trypsin, counted, suspended in M199 with 2 vol. % FBS, and seeded at 20,000 cells/$cm^2$ in 6-well plates pre-coated with gelatin. On day 1 of experiments, medium was aspirated from each well of 6-well plates and replaced with 1 mL of microsphere suspensions per well (for VEGF sequestering study). Alternately, microspheres in VEGF release study were centrifuged and only the supernatant (termed 'VEGF releasate') from each condition was added to HUVEC culture. HUVECs were incubated with microsphere suspensions (to examine the influence of VEGF sequestering) or VEGF releasate (to examine the influence of released VEGF) for 30 minutes at 37° C. The negative and positive controls consisted of 2 vol. % FBS in M199 without or with 10 ng/mL VEGF supplementation, respectively. Following 30-minute incubation, the wells of each 6-well plate were aspirated and washed with PBS, and 30 μL of 1× Sample Diluent Concentrate 2 (R&D Systems) supplemented with 10 μg/mL Aprotinin (Sigma), 10 μg/mL Leupeptin (Tocris), and 1×HALT Phosphatase Inhibitor (Thermo) was added to each well. HUVECs were subsequently scraped with a cell scraper, and cell lysate was placed in an Eppendorf tube on ice for 15 minutes before storage at −20° C. for at least 24 hours. Before assaying, cell lysates were centrifuged at 10,000×g for 10 minutes at 4° C. and stored on ice. Cell lysates were assayed for phosphorylated VEGFR2 using phospho-VEGFR2 ELISA (R&D Systems DYC1766) following standard protocol, using approximately 50 μg of cell lysate per sample per well. The total mass of phosphorylated VEGFR2 in each sample was determined by comparing the optical density (450 nm-540 nm) for each sample to a fresh standard curve performed in duplicate. The mass of phosphorylated VEGFR2 in each sample was normalized to total protein content in the cell lysate of each sample, determined using Micro BCA assay following standard procedure using approximately 5 μg of cell lysate per sample per well. Conditions were assayed in triplicate wells, and each well was assayed in duplicate for ELISA and Micro BCA assays.

Figure 6A:
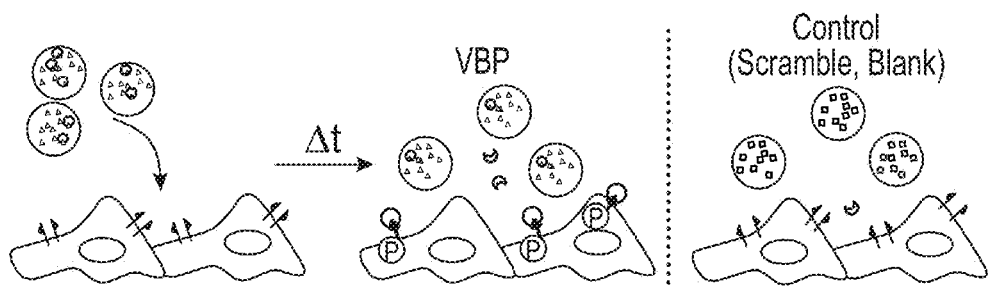
FIGS. 6A-6C show that VBP microspheres exhibited different effect on HUVEC metabolic activity upon VEGF release depending on crosslink identity.
Figure 6B:
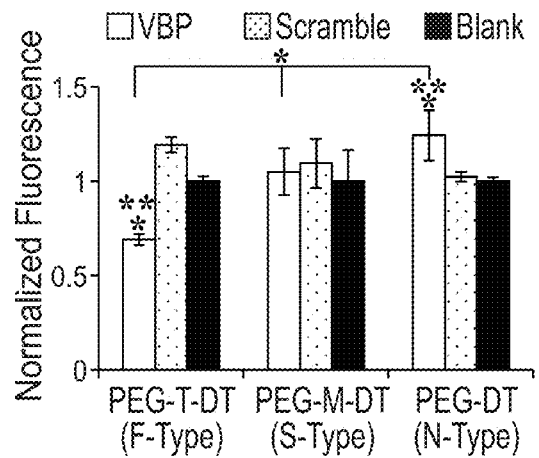
Figure 6C:
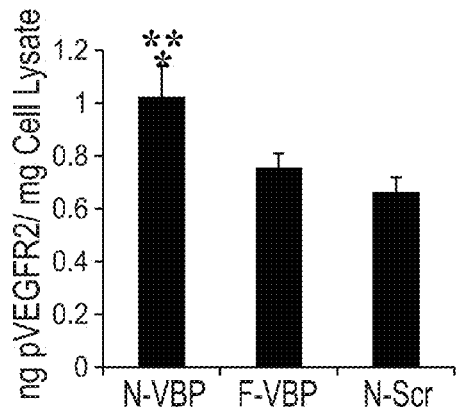

When VEGF was pre-loaded into VBP microspheres then added to cell culture, the degradation rate of VBP microspheres significantly influenced the activity of released VEGF (FIG. 6A). N-VBP microspheres preloaded with VEGF increased VEGF-dependent HUVEC metabolic activity upon VEGF release relative to N-Scramble and N-Blank microspheres (normalized data shown in FIG. 6B), which suggests that VEGF released from N-VBP microspheres was active. VEGF release from S-VBP microspheres exhibited no effect, as no differences were observed between S-VBP, S-Scramble, or S-Blank microsphere conditions, and the HUVEC metabolic activity upon VEGF release from S-VBP microspheres was significantly lower than from N-VBP microspheres (FIG. 6B). In contrast, VEGF release from F-VBP microspheres decreased VEGF-dependent HUVEC metabolic activity relative to F-Scramble and F-Blank microspheres and relative to S-VBP and N-VBP microspheres (FIG. 6B). Further, the VEGF released from N-VBP microspheres increased the levels of phosphorylated VEGFR2 in cultured HUVECs relative to N-Scramble or F-VBP microspheres, and VEGFR2 phosphorylation upon VEGF release from N-Scramble and F-VBP microspheres was indistinguishable (FIG. 6C). These data indicate that VEGF released from F-VBP microspheres was less active than that released from controls, S-VBP, or N-VBP microspheres and suggest that F-VBP microspheres reduced the activity of released VEGF.

Generation of Elastomeric Stencils for Endothelial Cell Sprouting Array

Sprouting arrays were generated using an elastomeric stencil. Polydimethylsiloxane (PDMS; Sylgard 184; Dow Corning) was prepared by mixing the curing agent at 10 vol. % in the base agent. PDMS with curing agent then was dispensed to 15 cm petri dishes (~15 g per dish), degassed for 30 minutes, and cured for 4 hours at 85° C. 64 wells (arranged in 16 groups of 4 as described below) were stamped out of each hardened PDMS stencil using 3 mm biopsy punch, and stencils were cleaned overnight using a Soxhlet extractor with hexanes. After cleaning, elastomeric stencils were placed at room temperature to remove residual solvent from the extraction and stored in 70 vol. % ethanol in DI water for sanitization before use.

Encapsulating iPSC-ECs in Cell-Dense Sphere

Hydrogel arrays were formed in two steps on subsequent days. Induced pluripotent stem cell-derived endothelial cells (iPSC-ECs; Cellular Dynamics International, Inc.) were expanded before use in Growth Medium containing 10 vol. % serum supplement (Cellular Dynamics International, Inc.), VEGF LifeFactors kit (LifeLine), penicillin/streptomycin, and VascuLife (LifeLine) and were used at passage 5 for experiments. On day 0 of experiments, iPSC-ECs were encapsulated in eight-arm PEG-norbornene hydrogels containing cell-adhesion peptide (CRGDS; GenScript) and matrix metalloproteinase-degradable crosslinker (KCGG-PQGIWGQGCK (SEQ ID NO:12); GenScript). iPSC-ECs were suspended at $8 \times 10^7$ cells/mL in 0.1 wt. % Irgacure 2959 (Ciba) in PBS and immediately diluted 1:1 in a 2× hydrogel precursor solution to make a final solution containing 4 wt. % eight-arm PEG-NB, 2 mM CRGDS (SEQ ID NO:11), 3.6 mM KCGGPQGIWGQGCK (SEQ ID NO:12). Cells were then encapsulated by exposing 0.5 μL cell-dense "spheres", formed at the end of a 10 μL pipet tip, to UV at 0.18 J/cm². iPSC-EC cell-dense spheres were cultured overnight in 16 well ProPlate (Grace Bio) slide chambers (with 64-well PDMS stencils installed in place of the 16-well silicone stencil) in Growth Medium at 37° C., 95% relative humidity, and 5% CO².

Impact of VEGF Sequestering on iPSC-EC Sprouting

On day 1 of experiments, iPSC-EC cell-dense spheres were surrounded by a synthetic ECM composed of eight-arm PEG-NB, CRGDS (SEQ ID NO:11), and KCGGPQGI-WGQGCK (SEQ ID NO:12) similarly to above with the addition of microspheres to the outer gel. Medium was aspirated from each well of the 64 well elastomeric stencil, and 10 μL of hydrogel precursor solution, consisting of 4 wt. % eight-arm PEG-NB, 2 mM CRGDS (SEQ ID NO:11), 3.6 mM KCGGPQGIWGQGCK (SEQ ID NO:12), 0.05 wt. % Irgacure 2959 in PBS, and 0 or 1 mg/mL of microspheres, was added to each well. Hydrogel arrays were polymerized at 0.09 J/cm², after which the 64 well PDMS stencil was replaced by a 16 well silicone stencil (Grace Bio), and medium consisting of 10 vol. % FBS, penicillin/streptomycin, VascuLife, and either 0 or 10 ng/mL VEGF was added to each well. The result of polymerization was four hydrogel posts, each with an encapsulated cell-dense sphere, within each well of the 16-well slide chamber. iPSC-EC arrays were then cultured for 6 days at 37° C., 95% relative humidity, and 5% $CO_2$ with medium replenished every other day. On day 6 of experiments, cells were stained with 2 μM Calcein-AM and 2 μM Ethidium homodimer-1 for 30 minutes at 37° C. After staining, iPSC-ECs were washed in PBS, fixed, and imaged. The extent of endothelial sprouting was assessed by counting the number of invading Calcein+ cells in the cell-free hydrogel using automated imaging on an epifluorescence microscope (Nikon Ti Eclipse) equipped with 4× objective and filters for phase contrast, TxRed, and FITC. Images were processed using NIS Elements v3.2 (Nikon). Conditions were assayed in replicates of eight and were compared using two-way ANOVA and post-hoc Student's t-test at $\alpha = 0.05$.

Figure 7A:
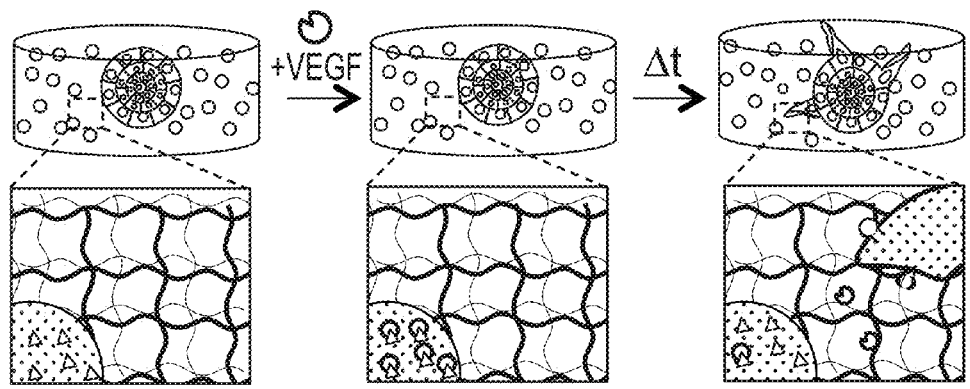
FIGS. 7A & 7B show the influence of VBP microspheres on induced pluripotent stem cell-derived endothelial cell (iPSC-EC) sprouting behavior in hydrogels.
Figure 7B:
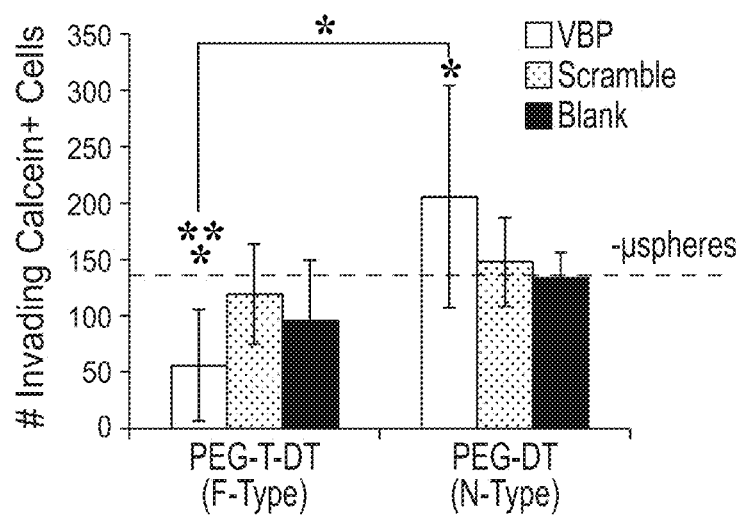

The influence of VBP microsphere degradation rate on stem cell-derived endothelial cell sprouting in synthetic hydrogels is shown in FIG. 7A. VBP microsphere degradation rate influenced the extent of VEGF-dependent iPSC-EC sprouting behavior in PEG-based synthetic hydrogels. In culture medium with soluble VEGF, encapsulated F-VBP microspheres significantly reduced iPSC-EC sprouting relative to F-Scramble microspheres and the no microsphere ('–μsphere') controls (FIG. 7B). Conversely, encapsulated N-VBP microspheres significantly increased iPSC-EC sprouting relative to the '–μsphere' control in culture with VEGF (FIG. 7B). Taken together, F-VBP microspheres reduced VEGFR2 phosphorylation and VEGF activity in culture with endothelial cells.

Impact of VEGF Sequestering on Angiogenesis in Mouse Choroidal Neovascularization Model Microspheres (generated via sonication) were sanitized either by washing in 70% ethanol or by exposing to UV for 30 minutes prior to injection. Microspheres (F-VBP, F-Scramble, N-VBP, and N-Scramble) were suspended at 2 mg/mL in sterile PBS on the day of experiments. Soluble VBP or Scramble peptide (purchased from GenScript) were dissolved, sterile filtered through 0.2 μm filter, and diluted to 20 μg/mL in sterile PBS before experiments. SU4312 (Sigma) was dissolved in DMSO at 5 μg/mL, and Eylea (Regeneron Pharmaceuticals) was dissolved in PBS at 40 μg/mL and sterile filtered through 0.2 μm filter.

Figure 8A:
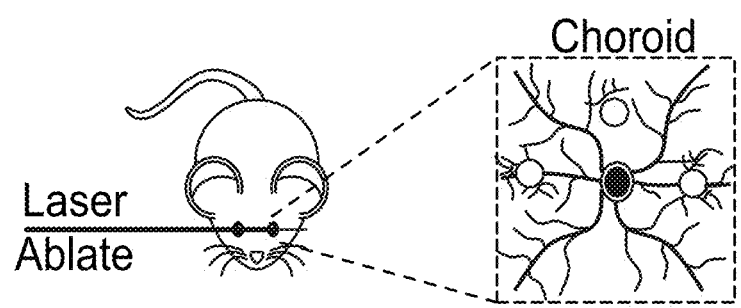
FIGS. 8A-8D show that degradable VBP microspheres reduced neovascularization in a mouse choroidal neovascularization model.

The mouse choroidal neovascularization model was generated as described in FIG. 8A. Briefly, C57BL/6J mice (Jackson Laboratories; 6-weeks old female) eyes were dilated using a drop of tropicamide (1%), and mice were anesthetized with ketamine and xylazine. Mice were subjected to photocoagulation (75 μm spot size, 0.1 s duration, 120 mW) at the 3-, 9-, and 12-o'clock positions of the posterior pole of the eye using an OcuLight GL diode laser (Iridex) with a glass coverslip over the eye. Microspheres were injected into each eye (2 μL/eye) using a pump microinjection apparatus (Harvard Apparatus) or Hamilton syringe. Similarly, for experiments with soluble peptide, Soluble VBP or Scramble were injected into each eye (2 μL/eye) using a pump microinjection apparatus. In separate experiments, soluble inhibitors (Vehicle or SU4312) or proteins (IgG or Eylea) were injected into each eye (2 μL/eye) using a pump microinjection apparatus. Mice were allowed to recover for 1 hour and housed for 7 days, whereupon the mice were subjected to a repeat injection of microspheres, soluble peptide, protein, or inhibitor (2 µL/eye). After an additional 7 days of housing, mice were euthanized, and eyes were isolated and fixed in 4 vol. % paraformaldehyde for 2 hours. Eyes were washed three times in PBS, divided at the equator, and the choroid and sclera of the posterior pole were isolated and blocked for 1 hour in 50 vol. % FBS. The isolated tissue (choroid and sclera) were stained with anti-intracellular adhesion molecule-2 (ICAM-2; BD Pharmingen) at 1:500 dilution in 20 vol. % FBS in PBS overnight. The tissues were subsequently washed three times in PBS and stained with secondary antibody. Tissues were washed three times in PBS, mounted with VectaMount AQ (Vector Laboratories), and imaged using epifluorescence microscopy (Zeiss). The area of ICAM-2+ staining (defined as mean CNV area) at each position (3-, 9-, and 12-o'clock) was quantified using Fiji and automated image thresholding. Outliers were identified and eliminated using the ROUT statistical method, and analysis was performed using one-way ANOVA with Tukey's post-hoc test and multiple comparisons correction ($\alpha=0.05$) in GraphPad Prism.

Figure 8B:
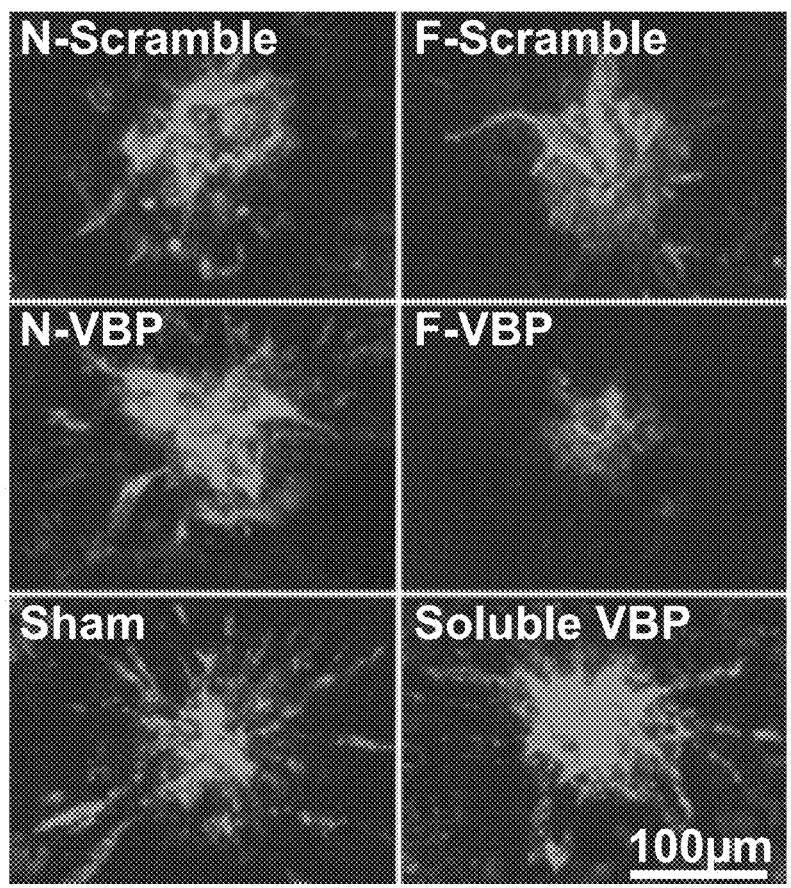
Figure 8C:
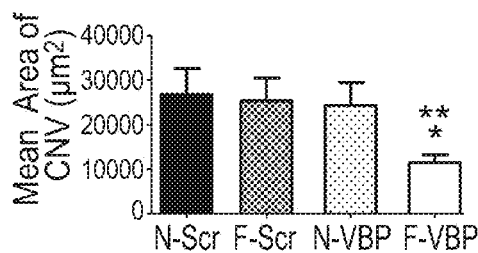
Figure 8D:
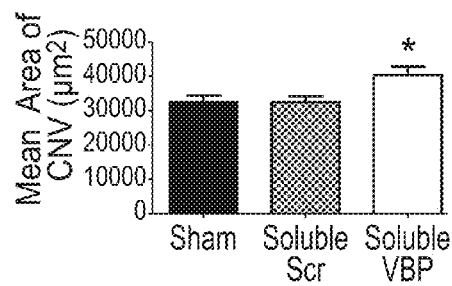
Figure 9:
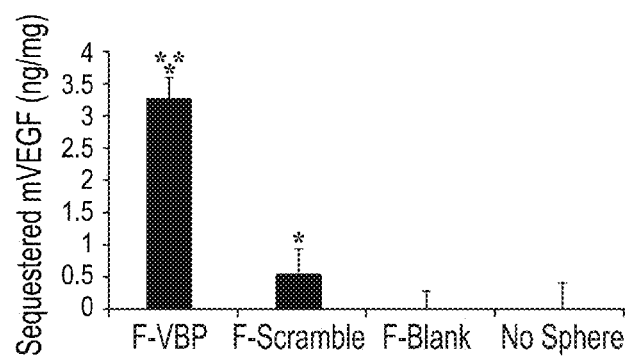
FIG. 9 is a graph showing that F-VBP microspheres sequestered murine VEGF. F-Type microspheres were assayed for binding murine VEGF164 (R&D Systems), hereafter referred to as mVEGF, by incubating microspheres in a solution containing 1 wt. % BSA in PBS with 10 ng/mL mVEGF for 4 hours at 37° C. After incubation, microspheres were centrifuged at 10,600×g for 5 minutes, and the supernatant was assayed with a mVEGF ELISA (R&D Systems) using the manufacturer's protocol. The concentration of mVEGF in the supernatant was correlated to the amount of mVEGF sequestered to the microspheres by subtracting the supernatant mVEGF concentration in each microsphere condition from the mVEGF concentration in the no microsphere condition (No Sphere). Data is presented as ng sequestered mVEGF per mg microspheres relative to the No Sphere condition. Error bars represent one standard deviation about the mean for three replicates. Asterisks denote statistical significance in Student's t-test relative to F-Blank (*) and F-Scramble (**) microspheres for p-value <0.05.
Figure 10A:
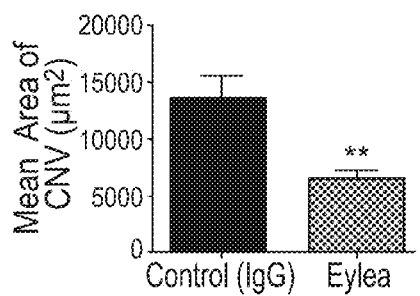
FIGS. 10A & 10B show the influence of soluble VEGF inhibitors on mean CNV area in mouse model. Data are presented as mean area of CNV in $\mu m^2$+/−one standard error of measurement (SEM) about the mean after treatment with (FIG. 10A) 40 μg/mL of IgG (Control) or Eylea or with (FIG. 10B) vehicle control (DMSO) or 5 μg/mL SU4312. Statistical significance relative to the control (black bars) in each respective experiment was determined using a Student's t-test and denoted for p-value<0.01 () or p-value<0.001 (*).
Figure 10B:
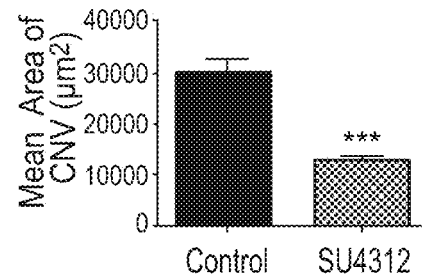

Injectable, degradable VBP microspheres reduced angiogenesis in a murine model of choroidal neovascularization in vivo (FIG. 8A). Choroidal neovascularization area was defined as the area of intracellular adhesion molecule 2 (ICAM-2) staining at each laser photocoagulation spot (FIG. 8B). Upon photocoagulation and intravitreal injection to mice, injected F-VBP microspheres reduced the mean choroidal neovascularization (CNV) area relative to F-Scramble microspheres and N-Scramble microspheres. In contrast, N-VBP microspheres did not significantly influence mean CNV area relative to N-Scramble or F-Scramble microspheres (FIG. 8C), indicating that microsphere degradation was critical to angiogenesis inhibition by VBP microspheres; thus, suggesting that a combination of VEGF sequestering to, and inactive VEGF release from, F-VBP microspheres led to inhibition of angiogenesis in vivo. To gain further insight into the effects of VBP on in vivo angiogenesis, the influence of soluble VBP on CNV area was also analyzed, and it was confirmed that neither soluble Scramble nor soluble VBP reduced CNV area relative to the saline 'Sham' control, though soluble VBP did significantly increase CNV area relative to Sham (FIG. 8D). Finally, the ability of F-VBP microspheres to sequester murine VEGF was confirmed (FIG. 9), which together suggests that F-VBP microspheres reduced choroidal neovascularization by virtue of VEGF sequestering and release of inactive VEGF. The ability of F-VBP microspheres to inhibit angiogenesis in this model was consistent with the effects of two commercial anti-angiogenesis compounds, Eylea and SU5416 (FIG. 10), which suggests potential therapeutic applications of injectable F-VBP microspheres.

In the foregoing Example, degradable VEGF sequestering hydrogel microspheres were prepared to provide a mechanism for temporally-controlled VEGF regulation. It was observed that the degradation rate of VEGF-sequestering microspheres strongly influenced the biological activity of VEGF in endothelial cell culture, and only VEGF-sequestering microspheres with inherent degradability reduced VEGF-dependent cell function in vitro and angiogenesis in vivo. These results highlight the ability to control growth factor activity in affinity-based biomaterials through modulating biomaterial degradability and demonstrate a potential therapeutic application of injectable, degradable VEGF-binding microspheres to reduce pathological angiogenesis in vivo.

Example 2

In this Example, VEGF-sequestering hydrogel microspheres used in the present disclosure were prepared and analyzed for their ability to regulate the activity of VEGF released from activated platelets.

Platelets contain an abundance of growth factors that mimic the composition of the wound healing milieu. Activated platelets release multiple pro-angiogenic growth factors simultaneously, and each of these factors can have unintended side effects if they are not provided within a narrow therapeutic concentration range. One illustrative example is VEGF, which is released by activated platelets and can negatively impact musculoskeletal wound healing if unregulated. In this Example, the microspheres were prepared and used to regulate the activity of VEGF released from activated platelets.

Materials and Methods

Peptide Synthesis

Protease activated receptor-1 activating peptide (PAR1AP), a VEGF-binding peptide (VBP) derived from VEGF receptor 2, a divalent VBP ($VBP_{2,linear}$) with the sequence KE{$F_d$}{$A_d$}{$Y_d$}{$L_d$}IDFNWEYPASKCKS APYEWNFDI{$L_d$}{$Y_d$}{$A_d$}{$F_d$}EK (SEQ ID NO:8), and a scrambled sequence of divalent VBP ($Scr_{2,linear}$) with the sequence KD{$A_d$}PYN{$F_d$}EFAWE{$Y_d$}IS{$L_d$}KCK {$L_d$}SI{$Y_d$}EWAFE{$F_d$}NYP{$A_d$}DK (SEQ ID NO:9) were synthesized using fmoc solid phase peptide synthesis using a microwave peptide synthesizer (Discover; CEM) and automated liquid handler (Liberty1; CEM). All amino acids and Rink Amide MBHA resin were purchased from EMD Novabiochem. Briefly, resin was swelled in N,N-dimethylformamide (DMF; Fisher) and deprotected in 20 vol. % piperidine (Sigma) and 0.1 M HOBt (Advanced Chem Tech) in DMF for 5 minutes under microwave at 70° C. Resin was washed twice in DMF before coupling, and the de-protected resin was mixed with four molar equivalents of amino acid (dissolved at 0.2 M in DMF) relative to free amines, four molar equivalents of HBTU (Advanced Chem Tech), and eight molar equivalents of diisopropylethylamine (DIPEA; Fisher), which was dissolved at 35 vol. % in N-methyl-2-pyrrolidone (Fisher). Coupling was performed for 5 minutes at 70° C. (Cysteine was coupled at 50° C.). Peptide purity was verified using reverse phase high performance liquid chromatography. Peptide identity was verified using time-of-flight mass spectroscopy (Bruker), and peptide content was determined using an Ellman's assay (Thermo Scientific) to measure free thiols.

Synthesis of PEG-Norbornene Microspheres

Four-arm poly(ethylene glycol) (PEG, Mn 20,000; Jenkem) terminated on each arm with hydroxyl groups was functionalized with norbornene using carbodiimide chemistry as described in Example 1. Microspheres containing no peptide (Blank), VBP, or Scramble were synthesized as described in Example 1 using an aqueous emulsion of a PEG-rich phase with 10 wt. % PEG-norbornene, half molar equivalent PEG dithiol (Mn=3,400; Laysan Bio) with respect to norbornene groups, photoinitiator (0.05% Irgacure 2959; Ciba), and either water or dissolved peptide (VBP, Scramble) at 0.016 molar equivalents with respect to norbornene, with a Dextran-rich phase containing 40 wt. % Dextran (Mn=40,000; Alfa Aesar) in KCl buffer. For microsphere synthesis with divalent peptides, peptides were first dissolved in DI water with added ammonium hydroxide (to facilitate dissolution) and were incorporated into microspheres at a ratio of 0 (Blank), 0.002 (0.2%), 0.008 (0.8%), and 0.063 (6.3%) molar equivalents with respect to norbornene. For all microsphere types, the PEG-rich phase was emulsified via vortexing for one minute in a six-fold volumetric excess of the Dextran-rich phase and was exposed to UV light (1.1 J/cm$^2$). Microspheres were washed in DI water and centrifuged at 1600×g, and the final product was then suspended in DI water, frozen in liquid nitrogen, and lyophilized. Peptide-containing microspheres were suspended in phosphate buffered saline (PBS; Fisher Scientific), and peptide content was verified using either Micro-BCA assay (Thermo Scientific) or by UV-Vis absorbance at 260 nm corresponding to the absorbance of tryptophan.

Platelet Activation

Expired platelet packs were donated from the University of Wisconsin Blood Bank, aliquoted, and stored at 4° C. for processing on the day of receipt. Platelet aliquots were centrifuged at 2000×g for 12 minutes, and the supernatant was collected and saved (referred to as "Plasma," P) or was used to re-suspend un-activated platelets (referred to as "Platelets+Plasma,", P+P). Platelets in treatment groups were suspended in HEPES buffer (0.2 M; pH 7.4; Fisher) at the same volume of Plasma that was removed. Platelets were then subjected to treatment with PAR1AP (0.1 M, 0.01M), Thrombin (0.4, 4 U/mL; Sigma Aldrich), CaCl$_2$ (0.5 wt. %; Fisher), or HEPES buffer (control) for 30 minutes at room temperature. Platelet suspensions in freeze/thaw treatment group were subjected to freezing three times in liquid nitrogen (5 minutes) and thawing in a 37° C. water bath (10 minutes). After activation, platelet suspensions were centrifuged at 2000×g for 10 minutes, and the supernatant (hereafter referred to as "platelet concentrate," PC) was sterile filtered through a 0.2 μm filter and collected for processing. Supernatants and controls were stored at −80° C. before ELISA was performed as described below.

Measurement of Growth Factors in Platelet Concentrate

Platelet Concentrate (PC) and both plasma (P) and platelets+plasma (P+P) controls were assayed for growth factor content using enzyme-linked immunosorbent assays (ELISA) for human Vascular Endothelial Growth Factor-165 (VEGF; R&D Systems DY293B), human Platelet-Derived Growth Factor-BB (PDGF-BB; R&D Systems DY220), or human Transforming Growth Factor β1 (TGFβ1; R&D Systems DY240) using standard assay procedure. The concentration of growth factor in each condition was calculated by comparing the corrected absorbance of each sample (450 nm-540 nm) to the standard curve generated in PBS. Samples and standard curves were assayed in triplicate. Statistical analysis was performed using one-way analysis of variance (ANOVA) with Bonferroni post-hoc test ($\alpha$=0.05).

Incubation of Microspheres with Platelet Concentrate

Platelets were activated using a freeze/thaw method as described above. Platelets for growth factor capture were suspended in PBS at one third of the volume of plasma removed to maximize the growth factor concentration in PC. After three freeze/thaw cycles, platelets were centrifuged as above, and the supernatant (PC) was sterile filtered and used to suspend microspheres at 1 mg/mL for 4 hours at 37° C. After incubation, microspheres were centrifuged at 10,600×g for 5 minutes, and the PC was subjected to the analysis methods below. For experiments with microspheres containing divalent peptides, $VBP_{2,linear}$ or $Scramble_{2,linear}$, platelets with plasma were activated by three freeze/thaw cycles and incubated directly with microspheres for 4 hours at 37° C. Subsequently, divalent peptide-containing microspheres and platelets were filtered before the filtrate was used for VEGF ELISA as described below.

Figure 11A:
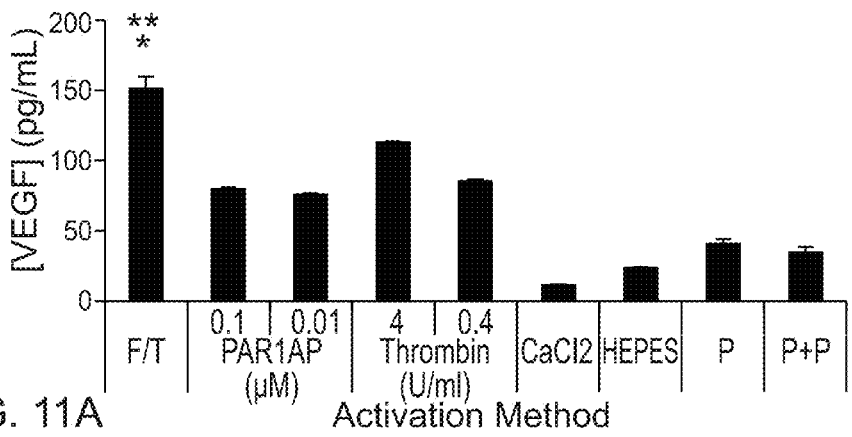
FIGS. 11A-11C depict the measurement of VEGF, PDGF-BB, and TGFβ1 present in platelet concentrate prepared by various methods. Quantification of VEGF165 (here referred to as VEGF) (FIG. 11A), PDGF-BB (FIG. 11B), and TGFβ1 (FIG. 11C) concentration in the supernatant of platelets prepared by the methods (described in Materials and Methods of Example 2) listed on the x-axis below each bar. Statistical comparisons were made using one-way ANOVA with Bonferroni post-hoc test and is shown for p-value<0.05 relative to 4 U/mL thrombin (**) or relative to all methods except thrombin (*). F/T=freeze/thaw, PAR1AP=protease activated receptor 1-activating peptide, P=plasma, P+P=platelets with plasma.
Figure 11B:
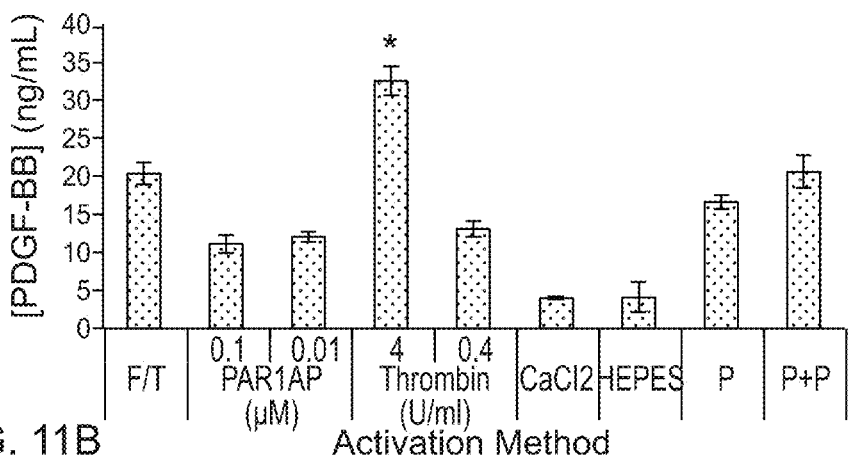
Figure 11C:
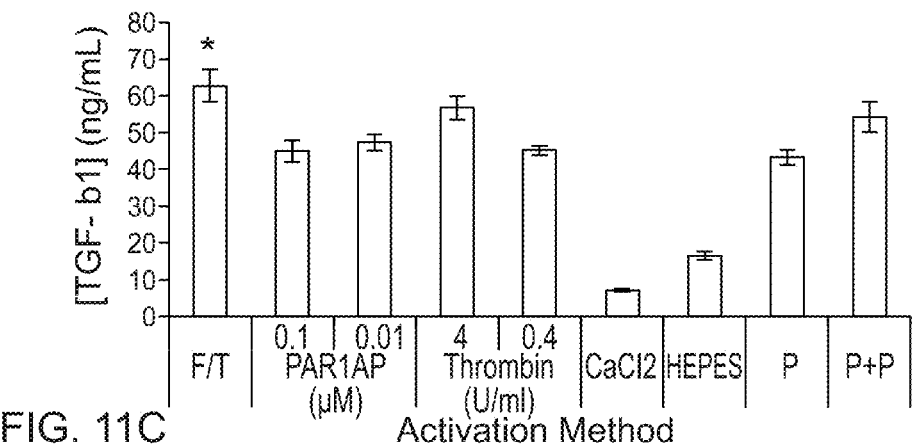

The relative growth factor concentrations in platelet concentrate (PC) varied depending on the method used for platelet activation: thrombin treatment, PAR1AP treatment, CaCl$_2$ treatment, or freeze/thaw. In particular, each activation method elicited different concentrations of three model growth factors that are critical during wound healing—VEGF-A (hereafter referred to as "VEGF"), PDGF-BB, and TGFβ1. Freeze/thaw resulted in a substantially higher concentration of released VEGF relative to all activation conditions (FIG. 11A) and a higher concentration of released TGFβ1 relative to all activation conditions except 4 U/mL Thrombin (FIG. 11C). 4 U/mL Thrombin resulted in the highest concentration of released PDGF-BB in PC relative to all other conditions (FIG. 11B). Substantially higher concentrations of each growth factor were present in PC generated using each technique relative to inactive platelets in the HEPES only control (FIGS. 11A-11C).

Figure 12A:
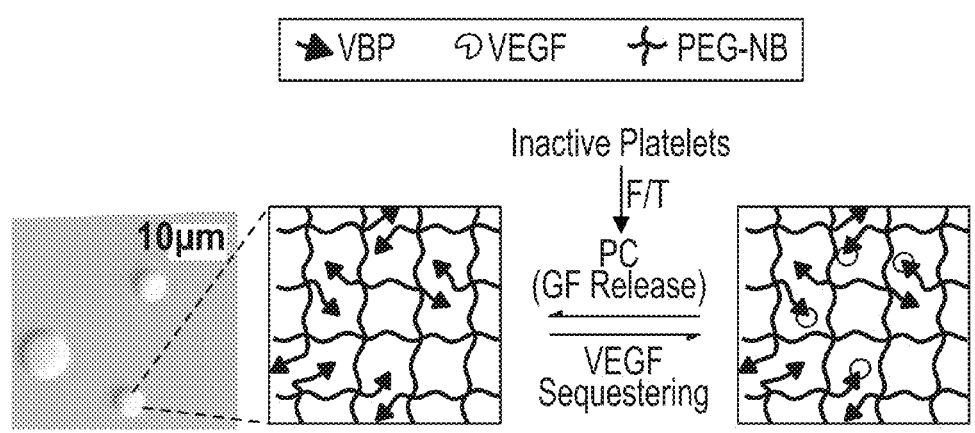
FIGS. 12A-12D show VBP microspheres sequestering VEGF from PC prepared via freeze/thaw.

Differences in growth factor released by each respective technique may be due to the differential capacity of each growth factor to bind to the fibrin clot produced during platelet activation. During freeze/thaw, no fibrin clot was formed, which suggests that each growth factor was not sequestered by fibrin and was thus soluble after freeze/thaw and centrifugation. Further, while freeze/thaw and thrombin activation techniques employed here released TGFβ1 at concentrations comparable to those previously reported, the concentration of PDGF-BB released here was almost one order of magnitude higher than previously reported. Literature supports the ability of freeze/thaw to maintain the immunoreactivity and activity of platelet-derived growth factors, and based on the observation that freeze/thaw produced the highest concentration of immunoreactive VEGF relative to the other activation conditions (FIG. 11A), freeze/thaw was used to generate PC for subsequent analysis of growth factor sequestering (FIG. 12A) and regulation.

ELISA Measurement of Growth Factors Sequestered from Platelet Concentrate

Microsphere supernatants as prepared above were subjected to VEGF ELISA as described above. For VEGF ELISA, the concentration of growth factor in the supernatant of each condition was correlated to the amount of bound VEGF by subtracting the concentration of VEGF in the supernatant of the no microsphere condition (NS) with the concentration of VEGF in the supernatant of each respective microsphere condition. Alternatively, the supernatants generated above were stored at −80° C. before being subjected to Human Angiogenesis/Growth Factor Magnetic Bead Panel (HAGP1MAG-12K; Millipore) as briefly described here following standard protocol. Briefly, the 96 well plate provided with the kit was washed in wash buffer, and subsequently samples (either un-diluted or diluted threefold in PBS) or standards (serially diluted in PBS) were incubated with antibody-conjugated beads and assay buffer overnight at 4° C. on a plate shaker. Beads were then washed in wash buffer, incubated with detection antibody cocktail for 1 hour at room temperature on a plate shaker, and incubated with streptavidin/phycoerythrin for 30 minutes at room temperature on a plate shaker. Finally, beads were washed with wash buffer and suspended in Magpix drive fluid (Life Technologies) for analysis on the Magpix Luminex XMAP (Life Technologies). Standard curves were analyzed using 4-PL analysis in GraphPad Prism, and median sample counts were correlated to standard curve using 4-PL interpolation to calculate a mean growth factor concentration for each dilution and microsphere condition. Data was aggregated from two separate readings of triplicate samples that were prepared at two different dilutions. Statistical analysis of the multiplexed ELISA was performed using one-way ANOVA with Fisher's least significant difference post-hoc test ($\alpha=0.01$), and plate-based ELISA data was analyzed using one-way ANOVA with Bonferroni post-hoc test ($\alpha=0.05$).

Figure 12B:
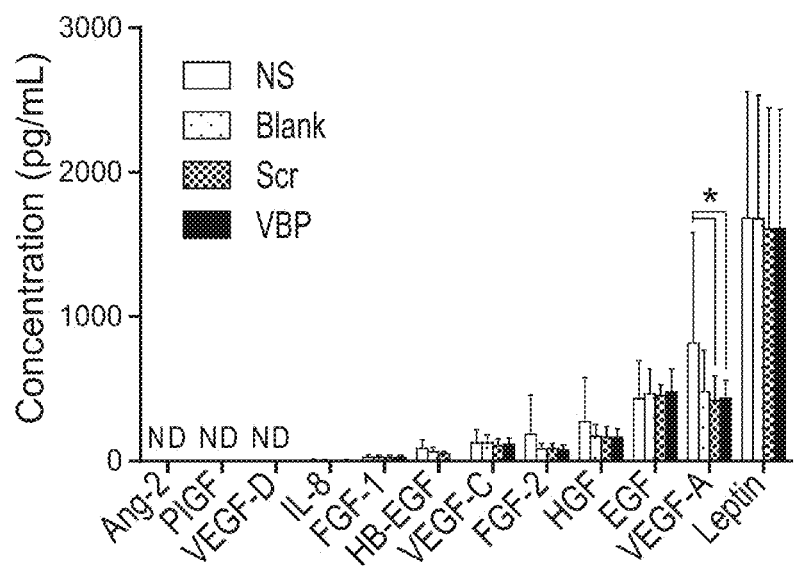

Microspheres containing VEGF-binding peptide motifs (VBP microspheres) specifically sequestered VEGF from PC. Analysis of the multiplexed ELISA data demonstrated that VBP microspheres sequestered VEGF from PC generated via freeze/thaw (FIG. 12B). Angiopoietin-2, Placental Growth Factor (PlGF), and Vascular Endothelial Growth Factor-D (VEGF-D) were not present in PC at detectable levels. While Interleukin-8 (IL-8), Heparin-Binding Epidermal Growth Factor-like Growth Factor (HB-EGF), Fibroblast Growth Factor-1 (FGF-1), and Hepatocyte Growth Factor (HGF) were present in PC at low concentrations in PC (<100 pg/ml), none of these growth factors showed detectable sequestering to any of the microsphere conditions evaluated (FIG. 12B). The PC incubated with or without microspheres also contained moderate levels of VEGF-C (~120 pg/mL), FGF-2 (~150 pg/mL), Epidermal Growth Factor (EGF) (~500 pg/mL), and Leptin (~1500 pg/mL), and none of these growth factors showed detectable sequestering to any of the microsphere conditions evaluated (FIG. 12B). The PC incubated with VBP microspheres and microspheres containing a scrambled version of VBP (Scramble) contained a significantly lower concentration of VEGF when compared to NS control, and the level of sequestered VEGF (~200 pg per mg microspheres) was on the order of the $ED_{50}$ of VEGF (100-200 pg/mL).

Figure 12C:
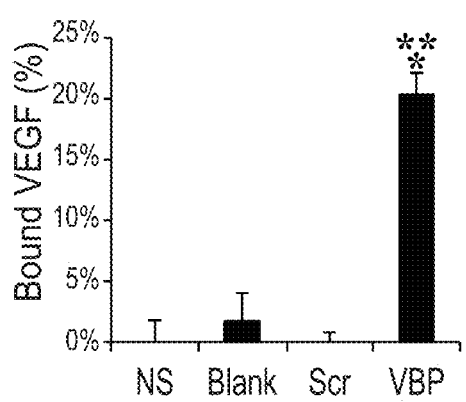

VBP microspheres sequestered significantly more VEGF from PC than Scramble or Blank microspheres. Specifically, VBP microspheres sequestered ~20% of the VEGF present in PC (relative to the NS control) (FIG. 12C). Neither Blank nor Scramble microspheres sequestered a significant amount of VEGF relative to the no microsphere (NS) control (FIG. 12C). The extent of VEGF sequestering to VBP microspheres here (~120 ng out of ~600 ng total VEGF in PC, or ~20% VEGF sequestering) is generally consistent with the ability of VBP microspheres to sequester ~40% of the recombinant VEGF in albumin-containing medium or 10-60% of the recombinant VEGF in serum-containing medium. These results demonstrate that VBP microspheres sequestered VEGF with specificity, and it was further hypothesized that VBP microspheres would influence VEGF activity in PC without influencing the activity of other pro-angiogenic platelet-derived GFs.

Regulation of the Activity of VEGF Captured from PC

Human umbilical vein endothelial cells (Lonza) were expanded under normal culture conditions (37° C., 5% $CO_2$) in medium 199 (M199; CellGro) supplemented with EGM-2 BulletKit (Lonza) and penicillin/streptomycin (P/S; Gibco) and were used at passage 4 for experiments. On the day before experiments, HUVECs were seeded overnight under normal culture conditions onto 96 well plates, which were pre-coated with fibronectin (Corning), at 4000 cells/well in M199 supplemented with 2 vol. % fetal bovine serum (FBS; Gibco) and P/S. On the day of experiments, microspheres (VBP, Scramble, and Blank) were sanitized with 70 vol. % ethanol (Fisher) in DI water for 1 hour and washed with PBS prior to use. PC was generated as described above using freeze/thaw, and microspheres were subsequently incubated in either 0.1% BSA in PBS or PC at 1 mg/mL microspheres for 3 hours at 37° C. Microspheres were centrifuged at 1600×g for 5 minutes and washed for 1 hour in 0.1% BSA in PBS for 1 hour at 37° C. Microspheres were again centrifuged at 1600×g for 5 minutes and subsequently suspended at 5 mg/mL in M199 supplemented with 2 vol. % FBS and P/S. Medium from HUVEC culture was replaced with microsphere suspensions, and HUVECs were cultured with microspheres for 48 hours under normal culture conditions in the presence of 10 µM EdU (Thermo Scientific). After 48 hours, HUVECs were fixed in formalin (Fisher), stained with AlexaFluor 594, and counter-stained with Hoechst using standard Click-iT EdU (Thermo Scientific) assay protocol. The mean fraction of EdU+/Hoechst+ cells was tabulated for 6 replicate well per condition, and statistical analysis was performed using one-way ANOVA and Dunnett's post-hoc test or two-way ANOVA ($\alpha=0.05$).

Figure 12D:
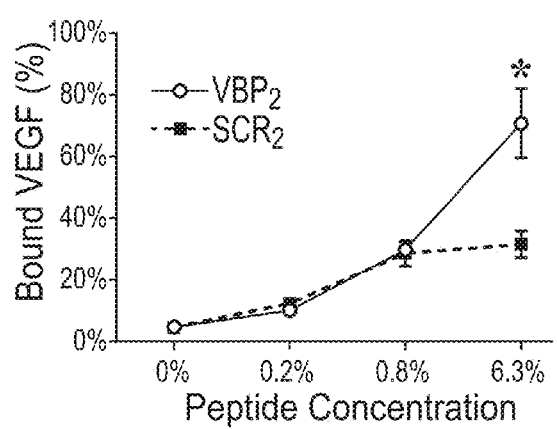
Figure 13A:
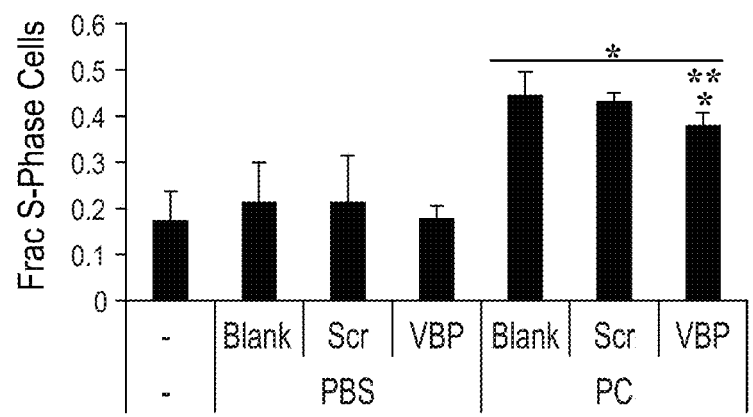
FIGS. 13A & 13B show that VBP microspheres reduced HUVEC proliferation after incubating in PC.
Figure 13B:
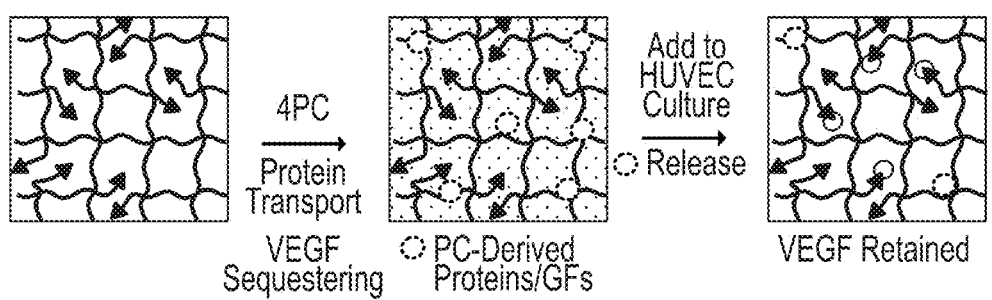
Figure 14A:
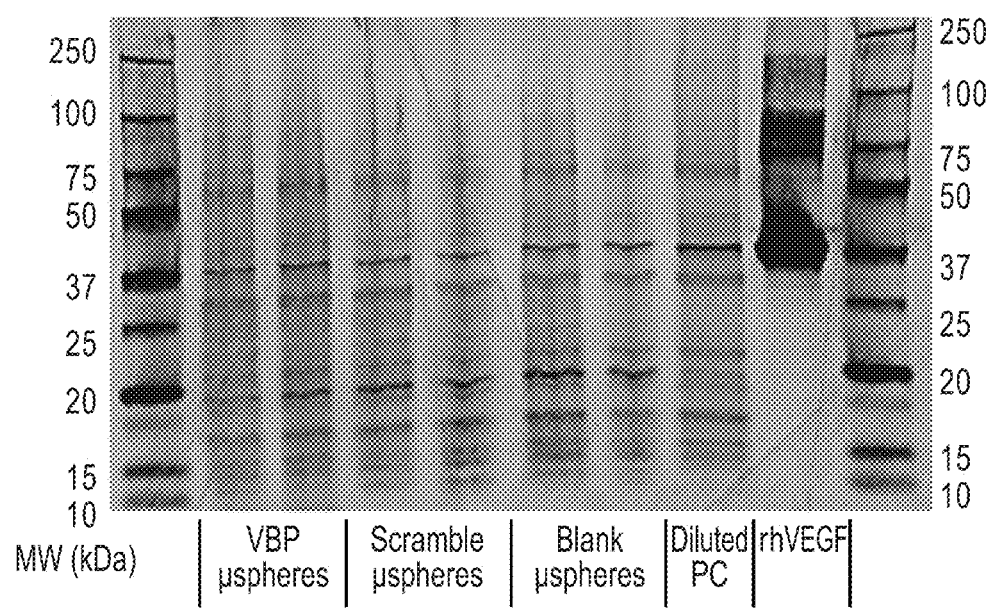
FIG. 14A is a SDS-PAGE gel of microspheres (μspheres) after incubation in PC, brief washing, and treatment with Laemli buffer (under non-reducing conditions). After incubation of microspheres (VBP, Scramble, and Blank) with PC as described above, 1 mg microspheres per condition were briefly washed in PBS and suspended in 25 μL PBS and 25 μL Laemli buffer (Biorad) without (3-mercaptoethanol (non-reducing conditions) at 55° C. for 10 minutes. Control conditions consisted of diluted PC in PBS, recombinant VEGF control (R&D Systems, 100 ng/mL in 0.1 wt. % BSA in PBS), and protein ladder (Biorad) diluted 10-fold in PBS. Subsequently, microsphere suspensions and controls were loaded at 10 μL per well into the wells of a 4-15% gradient Mini Protean TGX precast polyacrylamide gel (Biorad). Gels were then placed in a Biorad electrophoresis chamber which was filled with a running buffer (25 mM Tris-HCl, 192 mM Glycine, 0.1% SDS), and gels were run at 110V for 55 minutes. Subsequently, standard silver stain protocol was performed (GE Healthcare Protein Silver Stain Kit), and the stained gel was imaged using a standard 8 MP camera with backlighting. Subsequent staining with SilverStain demonstrated the presence of several unique proteins that were present in all microsphere types after incubation with PC.
Figure 14B:
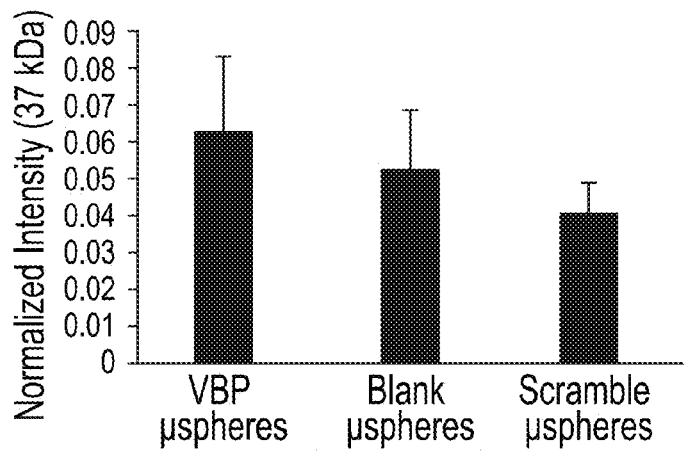
FIG. 14B depicts densitometry analysis in ImageJ of SDS-PAGE band at 37 kDa, which corresponds to the expected molecular weight of VEGF in non-reducing conditions and to the experimental molecular weight of recombinant VEGF in control (rhVEGF). The intensity of all 37 kDa band in each lane was normalized to the sum of intensity of all peaks (from 10 kDa to 250 kDa). The data are presented as the mean normalized intensity+/−one standard deviation for two lanes per condition. No statistical significance was observed between conditions using one-way ANOVA and Tukey's post-hoc test (p-value >0.05).

VBP reduced the influence of PC-loaded microspheres on HUVEC proliferation, indicating that VEGF sequestering from PC was biologically significant. Culture with microspheres pre-incubated in PC resulted in an increased fraction of HUVECs in S-phase when compared to culture with microspheres pre-incubated in PBS and to the no VEGF control (FIG. 13A). VBP microspheres pre-incubated in PC reduced HUVEC proliferation relative to both Scramble and Blank microspheres pre-incubated in PC (FIG. 13A). This result agrees with a previous study, which demonstrated that VBP microspheres reduced HUVEC proliferation in culture with recombinant VEGF. It is hypothesized that microspheres increased HUVEC proliferation after incubation with PC as a result of mass transport of PC-derived proteins into hydrogel microspheres (FIG. 13B). The presence of several unique proteins (including a protein band consistent with VEGF at approximately 37 kDa) that were present in all microsphere types after incubation with PC (FIG. 14A) were confirmed, which suggests that several PC-derived proteins were present in microspheres after incubation with PC, released into HUVEC culture, and stimulated HUVEC proliferation. However, densitometry analysis of the normalized intensity of the 37 kDa protein band did not result in statistical differences between VBP, Scramble, and Blank microspheres (FIG. 14B). This data together suggest a mechanism whereby PC-derived proteins (including VEGF) diffused into all microsphere types (FIG. 13B) and stimulated HUVEC proliferation upon release in culture, while VBP microspheres sequestered significantly more VEGF than controls (FIGS. 12B-12D) and reduced the amount of soluble VEGF in culture.

Finally, previous results have demonstrated that microspheres containing divalent VBP sequestered VEGF to a greater extent and with higher affinity than microspheres containing monomeric VBP0, and thus it was hypothesized that this approach could be used to increase the efficiency of VEGF sequestering from PC. Platelets were activated (with plasma) via freeze/thaw, and it was demonstrated that VEGF sequestering to microspheres containing a high concentration of divalent VBP, $VBP_{2,linear}$, was significantly higher (~80%) than sequestering to $Scr_{2,linear}$ microspheres (~30%) or Blank microspheres (~5%) (FIG. 12D). This result suggests that microspheres containing divalent growth factor-binding peptides may efficiently bind and potently reduce the activity of particular endogenous growth factors.

CONCLUSION

As found in the present Example, a platelet freeze/thaw cycle produced higher levels of VEGF than treatment with thrombin, PAR1AP, or calcium chloride. Further, given the abundance of VEGF in platelets and the need to tightly regulate VEGF activity during wound healing, a means of specifically sequestering and regulating platelet-derived VEGF was needed. Using the PEG microspheres, it was found that, out of a panel of 9 measured growth factors in platelet concentrate, VBP microspheres sequestered primarily VEGF, and VBP microspheres pre-incubated in platelet concentrate reduced HUVEC proliferation relative to controls.

Example 3

In this Example, the ability of microspheres prepared with linear VBP dimer peptides for sequestering VEGF was compared to that of microspheres prepared with branched VBP dimer peptides.

Particularly, PEG microspheres covalently linked to either linear VBP dimer peptide (KE$\{F_d\}\{A_d\}\{Y_d\}\{L_d\}$IDFNWEYPASKCKSAPYEWNFDI$\{L_d\}\{Y_d\}\{A_d\}\{F_d\}$EK (SEQ ID NO:9) or the branched VBP dimer peptide (E$\{F_d\}\{A_d\}\{Y_d\}\{L_d\}$IDFNWEYPASK)$_2$KC (SEQ ID NO:4)) were prepared as described above. The ability of each of the microspheres to sequester VEGF was analyzed as described above.

Figure 15A:
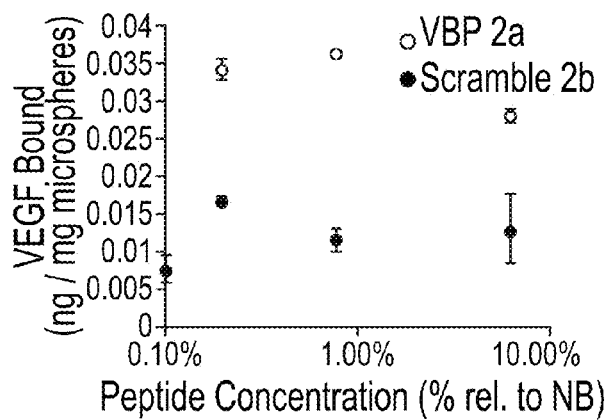
FIGS. 15A & 15B depict VEGF sequestering to microspheres functionalized with branched VBP dimer peptides (FIG. 15A) or linear VBP dimer peptides (FIG. 15B). Briefly, microspheres containing $VBP_{2,a}$, $Scramble_{2,b}$, $VBP_{2,linear}$, or $Scramble_{2,\ linear}$, were prepared and incubated in a solution containing 0.1 wt. % BSA in PBS, 9.9 ng/mL VEGF, and 0.1 ng/mL[$I^{125}$]VEGF for 4 hours at 37° C. After incubation, microspheres were centrifuged at 12,000×g for 5 minutes, and the supernatant was assayed for VEGF content using a γ counter, and supernatant counts per minute (CPM) were compared to a standard curve to calculate the concentration of VEGF in the supernatant of each condition. The amount of bound VEGF was calculated by subtracting the concentration of VEGF in the supernatant of the no microsphere condition with the concentration of VEGF in the supernatant of each microsphere condition.
Figure 15B:
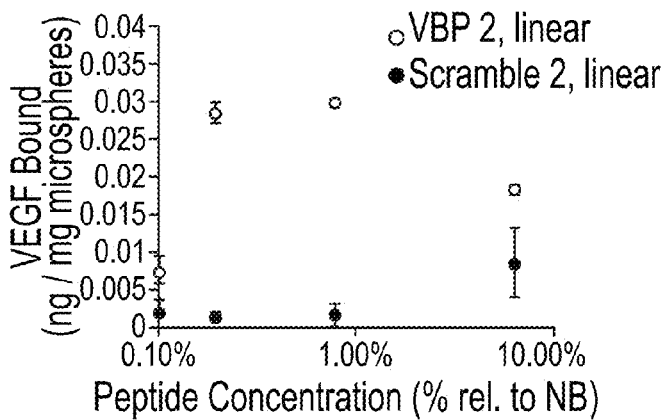
Figure 16:
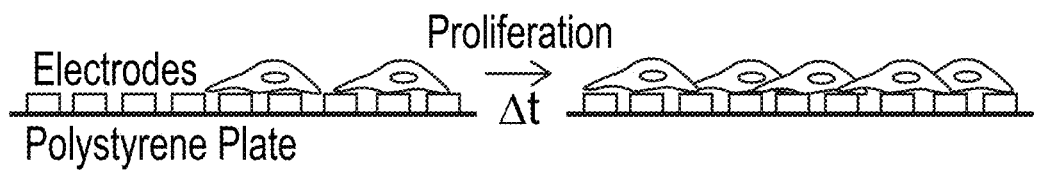
FIG. 16 is a schematic of iPSC-EC proliferation as assessed by taking measurements of impedance (normalized to generate a cell index) of gold-plated microscope slides seeded with iPSC-EC.

As shown in FIGS. 15A & 15B, both branched and linear VBP sequester VEGF specifically (relative to the scramble and blank, show at '0.1%' on x-axis). Non-specific binding to scrambled linear VBP (Scramble2, linear, however, was found to be lower than in the scrambled branched VBP (Scramble2,b).

Example 4

In this Example, the influence of soluble branched VBP on iPSC-EC Proliferation was analyzed.

Soluble branched VBP containing a PEG-27 spacer (C$\{\beta A\}$K($\{\beta A\}$$\{$PEG-27$\}$KSAPYEWNFDI$\{L_d\}\{Y_d\}\{A_d\}\{F_d\}$E)$_2$ (SEQ ID NO:10) was synthesized as described above using fmoc solid-phase peptide synthesis, wherein each amino acid after the branch point was added at 8 molar excess relative to the resin free amines with a corresponding 8 molar excess of DIPEA and 4 molar excess of HBTU during the coupling reaction. Peptide purity was assessed using reverse-phase high performance liquid chromatograph, and peptide identity was assessed using matrix-assisted laser desorption time-of-flight spectrometry. Peptide content was assessed using Ellman's assay for free thiol, and both soluble branched VBP$_{2, PEG-27}$ and VBP$_{2,a}$ were dissolved in PBS for use in cell culture assay. The influence of soluble branched peptides on iPSC-EC proliferation was established using ACEA xCELLigence RTCA-DP. iPSC-EC used in this Example were cultured in iCell-EC Growth Medium (as described in Example 1 above), were passaged using TrypLE, and were used between passage 4-8 for experiments. E-plates (containing gold electrodes on the bottom of each well) were first coated with Fibronectin (Corning) and were seeded with iPSC-EC at a density of 6000 cells/cm$^2$. Seeded E-plates were cultured on RTCA-DP overnight in Growth Medium, and on the day of experiments, medium was removed and replaced with medium containing 0.1 vol % supplement (CDI) in VascuLife (LifeLine) and L-glutamine (LifeLine) and containing 5 ng/mL VEGF (LifeLine) and the specified concentrations of either VBP$_{2, PEG-27}$ or VBP$_{2,a}$. iPSC-EC proliferation was assessed by monitoring the cell index (indicating cell coverage over the gold-coated wells) over a 48-hour period in culture, and at the end of the 48-hour culture, cell indices were averaged for two replicate wells per condition. Statistical analysis at the end of the experiment was performed using two-way analysis of variance (ANOVA) and Tukey's post-hoc test for $\alpha$=0.05.

Figure 17:
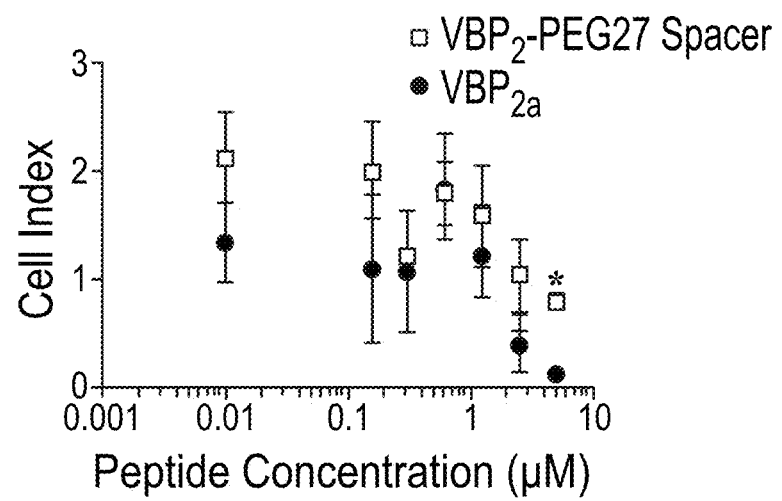
FIG. 17 depicts the influence of several concentrations of soluble branched VBP (with PEG spacer) on iPSC-EC proliferation as measured by calculating the cell index, which is proportional to the cell coverage on gold-coated wells.
Figure 18A:
FIGS. 18A-18D show that microsphere diameter is influenced by emulsion conditions as described in Example 1.
Figure 18B:
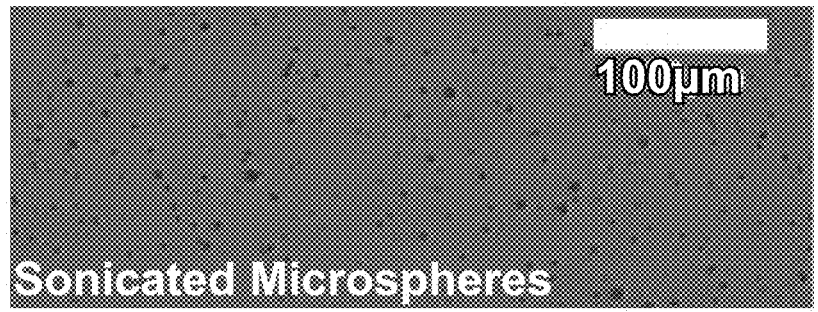
Figure 18C:
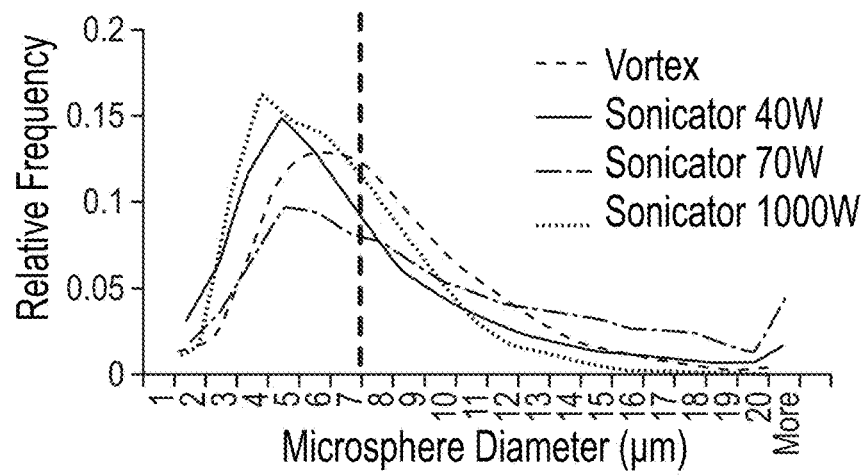
Figure 18D:
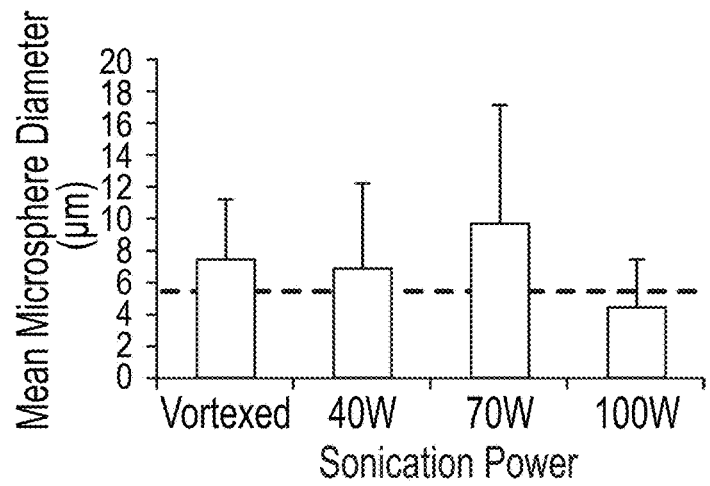

As shown in FIG. 17, both branched peptides inhibited iPSC-EC proliferation in culture with VEGF (ANOVA p-value <0.05), but VBP2,a inhibited proliferation at a much greater extent than the VBP2, PEG27 at 5 µM (shown by asterisk for p-value <0.05 using Tukey's post-hoc test)

---

What is claimed is:

1. A method of reducing vascular endothelial growth factor (VEGF) in a blood product of a subject in need thereof, the method comprising contacting a VEGF-sequestering hydrogel microsphere with the blood product, the VEGF-sequestering hydrogel microsphere comprising a polymeric degradable microsphere covalently linked to a VEGF-binding peptide derived from vascular endothelial growth factor receptor 2 (VEGFR2), the VEGF-binding peptide being selected from the group consisting of SEQ ID NO:8 and SEQ ID NO:10.

2. The method as set forth in claim 1, wherein the polymeric microsphere comprises a polymer selected from the group consisting of poly(ethylene glycol) (PEG), polyamidoamine, polyglycerol, poly(e-oxazoline), poly(N-isopropylacrylamide), hyaluronic acid, dextran, alginate, gelatin, and combinations thereof.

3. The method as set forth in claim 1, wherein the polymeric microsphere comprises PEG.

4. The method as set forth in claim 1, wherein the VEGF-sequestering hydrogel microsphere has a particle size ranging from 5 μm to about 10 μm.

5. The method as set forth in claim 1, wherein the blood product is selected from the group consisting of platelet lysate and platelet-rich plasma.

6. The method as set forth in claim 1, wherein the blood product is an autologous blood product.

7. A method of administering a blood product having reduced vascular endothelial growth factor (VEGF) to a subject in need thereof, the method comprising:
preparing a blood product;
contacting a VEGF-sequestering hydrogel microsphere with the blood product to reduce VEGF in the blood product, the VEGF-sequestering hydrogel microsphere comprising a polymeric degradable microsphere covalently linked to a VEGF-binding peptide derived from vascular endothelial growth factor receptor 2 (VEGFR2), the VEGF-binding peptide being selected from the group consisting of SEQ ID NO:8 and SEQ ID NO:10; and
administering the blood product with reduced VEGF to the subject.

8. The method as set forth in claim 7, wherein the blood product is obtained from the same subject that will be administered the blood product with reduced VEGF.

9. The method as set forth in claim 7, wherein the blood product is selected from the group consisting of platelet lysate and platelet-rich plasma.

10. The method as set forth in claim 7, wherein the polymeric microsphere comprises a polymer selected from the group consisting of poly(ethylene glycol) (PEG), polyamidoamine, polyglycerol, poly(e-oxazoline), poly(N-isopropylacrylamide), hyaluronic acid, dextran, alginate, gelatin, and combinations thereof.

11. The method as set forth in claim 7, wherein the polymeric microsphere comprises PEG.

12. The method as set forth in claim 7, wherein the VEGF-sequestering hydrogel microsphere has a particle size ranging from 5 μm to about 10 μm.

13. A method of reducing vascular endothelial growth factor (VEGF) in a blood product of a subject in need thereof, the method comprising contacting a VEGF-sequestering hydrogel microsphere with the blood product, the VEGF-sequestering hydrogel microsphere comprising an 8-arm, 20 kDa polyethylene glycol functionalized with norbornene covalently linked to a VEGF-binding peptide derived from vascular endothelial growth factor receptor 2 (VEGFR2), the VEGF-binding peptide being selected from the group consisting of SEQ ID NO:8 and SEQ ID NO:10.

* * * * *

SEQUENCE LISTING

```
<160> NUMBER OF SEQ ID NOS: 12

<210> SEQ ID NO 1
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(6)
<223> OTHER INFORMATION: D-amino acids

<400> SEQUENCE: 1

Cys Glu Phe Ala Tyr Leu Ile Asp Phe Asn Trp Glu Tyr Pro Ala Ser
1               5                   10                  15

Lys

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Cys Glu Leu Asn Val Gly Ile Asp Phe Asn Trp Glu Tyr Pro Ala Ser
1               5                   10                  15
```

Lys

<210> SEQ ID NO 3
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (13)..(13)
<223> OTHER INFORMATION: D-amino acid
<220> FEATURE:
<221> NAME/KEY: MISC_FEATURE
<222> LOCATION: (16)..(16)
<223> OTHER INFORMATION: D-amino acid

<400> SEQUENCE: 3

Cys Asp Ala Pro Tyr Asn Phe Glu Phe Ala Trp Glu Tyr Ile Ser Leu
1               5                   10                  15

Lys

<210> SEQ ID NO 4
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: D-amino acids
<220> FEATURE:
<221> NAME/KEY: MISC_FEATURE
<222> LOCATION: (18)..(21)
<223> OTHER INFORMATION: D-amino acids

<400> SEQUENCE: 4

Glu Phe Ala Tyr Leu Ile Asp Phe Asn Trp Glu Tyr Pro Ala Ser Lys
1               5                   10                  15

Glu Phe Ala Tyr Leu Ile Asp Phe Asn Trp Glu Tyr Pro Ala Ser Lys
                20                  25                  30

Lys Cys

<210> SEQ ID NO 5
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<220> FEATURE:
<221> NAME/KEY: MISC_FEATURE
<222> LOCATION: (17)..(20)
<223> OTHER INFORMATION: D-amino acids

<400> SEQUENCE: 5

Glu Phe Ala Tyr Leu Ile Asp Phe Asn Trp Glu Tyr Pro Ala Ser Glu
1               5                   10                  15

```
Phe Ala Tyr Leu Ile Asp Phe Asn Trp Glu Tyr Pro Ala Ser Lys Lys
        20                  25                  30

Lys Cys

<210> SEQ ID NO 6
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (12)..(12)
<223> OTHER INFORMATION: D-amino acid
<220> FEATURE:
<221> NAME/KEY: MISC_FEATURE
<222> LOCATION: (15)..(15)
<223> OTHER INFORMATION: D-amino acid
<220> FEATURE:
<221> NAME/KEY: MISC_FEATURE
<222> LOCATION: (18)..(18)
<223> OTHER INFORMATION: D-amino acid
<220> FEATURE:
<221> NAME/KEY: MISC_FEATURE
<222> LOCATION: (22)..(22)
<223> OTHER INFORMATION: D-amino acid
<220> FEATURE:
<221> NAME/KEY: MISC_FEATURE
<222> LOCATION: (28)..(28)
<223> OTHER INFORMATION: D-amino acid
<220> FEATURE:
<221> NAME/KEY: MISC_FEATURE
<222> LOCATION: (31)..(31)
<223> OTHER INFORMATION: D-amino acid

<400> SEQUENCE: 6

Asp Ala Pro Tyr Asn Phe Glu Phe Ala Trp Lys Tyr Ile Ser Leu Glu
1               5                   10                  15

Asp Ala Pro Tyr Asn Phe Glu Phe Ala Trp Lys Tyr Ile Ser Leu Glu
        20                  25                  30

Lys Cys

<210> SEQ ID NO 7
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: D-amino acids
<220> FEATURE:
<221> NAME/KEY: MISC_FEATURE
<222> LOCATION: (17)..(20)
<223> OTHER INFORMATION: D-amino acids

<400> SEQUENCE: 7

Glu Phe Ala Tyr Leu Ile Asp Phe Asn Trp Glu Tyr Pro Ala Ser Glu
1               5                   10                  15

Phe Ala Tyr Leu Ile Asp Phe Asn Trp Glu Tyr Pro Ala Ser Lys Cys
        20                  25                  30
```

```
<210> SEQ ID NO 8
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(6)
<223> OTHER INFORMATION: D-amino acids
<220> FEATURE:
<221> NAME/KEY: MISC_FEATURE
<222> LOCATION: (30)..(33)
<223> OTHER INFORMATION: D-amino acids

<400> SEQUENCE: 8

Lys Glu Phe Ala Tyr Leu Ile Asp Phe Asn Trp Glu Tyr Pro Ala Ser
1               5                   10                  15

Lys Cys Lys Ser Ala Pro Tyr Glu Trp Asn Phe Asp Ile Leu Tyr Ala
            20                  25                  30

Phe Glu Lys
        35

<210> SEQ ID NO 9
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<220> FEATURE:
<221> NAME/KEY: MISC_FEATURE
<222> LOCATION: (7)..(7)
<220> FEATURE:
<221> NAME/KEY: MISC_FEATURE
<222> LOCATION: (13)..(13)
<220> FEATURE:
<221> NAME/KEY: MISC_FEATURE
<222> LOCATION: (16)..(16)
<220> FEATURE:
<221> NAME/KEY: MISC_FEATURE
<222> LOCATION: (20)..(20)
<220> FEATURE:
<221> NAME/KEY: MISC_FEATURE
<222> LOCATION: (23)..(23)
<220> FEATURE:
<221> NAME/KEY: MISC_FEATURE
<222> LOCATION: (33)..(33)

<400> SEQUENCE: 9

Lys Asp Ala Pro Tyr Asn Phe Glu Phe Ala Trp Glu Tyr Ile Ser Leu
1               5                   10                  15

Lys Cys Lys Leu Ser Ile Tyr Glu Trp Ala Phe Glu Phe Asn Tyr Pro
            20                  25                  30

Ala Asp Lys
        35

<210> SEQ ID NO 10
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Beta-alanine
```

```
<220> FEATURE:
<221> NAME/KEY: MISC_FEATURE
<222> LOCATION: (4)..(4)
<223> OTHER INFORMATION: Beta-alanine
<220> FEATURE:
<221> NAME/KEY: MISC_FEATURE
<222> LOCATION: (4)..(5)
<223> OTHER INFORMATION: polyethylene glycol 27 spacer
<220> FEATURE:
<221> NAME/KEY: MISC_FEATURE
<222> LOCATION: (16)..(19)
<223> OTHER INFORMATION: D-amino acids
<220> FEATURE:
<221> NAME/KEY: MISC_FEATURE
<222> LOCATION: (21)..(21)
<223> OTHER INFORMATION: Beta-alanine
<220> FEATURE:
<221> NAME/KEY: MISC_FEATURE
<222> LOCATION: (21)..(22)
<223> OTHER INFORMATION: polyethylene glycol 27 spacer
<220> FEATURE:
<221> NAME/KEY: MISC_FEATURE
<222> LOCATION: (33)..(36)
<223> OTHER INFORMATION: D-amino acids

<400> SEQUENCE: 10

Cys Ala Lys Ala Lys Ser Ala Pro Tyr Glu Trp Asn Phe Asp Ile Leu
1               5                   10                  15

Tyr Ala Phe Glu Ala Lys Ser Ala Pro Tyr Glu Trp Asn Phe Asp Ile
            20                  25                  30

Leu Tyr Ala Phe Glu
        35

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Cys Arg Gly Asp Ser
1               5

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

Lys Cys Gly Gly Pro Gln Gly Ile Trp Gly Gln Gly Cys Lys
1               5                   10
```